(12) United States Patent
Schulze et al.

(10) Patent No.: US 11,530,201 B2
(45) Date of Patent: Dec. 20, 2022

(54) TRIAZINE COMPOUNDS SUBSTITUTED WITH BULKY GROUPS

(71) Applicants: Novaled GmbH, Dresden (DE); Samsung SDI Co., Ltd., Gyeonggi-do (KR)

(72) Inventors: Benjamin Schulze, Dresden (DE); Ansgar Werner, Dresden (DE); Elena Galan, Dresden (DE); Regina Luschtinetz, Dresden (DE); Qiang Huang, Dresden (DE); Kipo Jang, Gyeonggi-do (KR); Hyungsun Kim, Gyeonggi-do (KR)

(73) Assignees: Novaled GmbH, Dresden (DE); Samsung SDI Co. Ltd., Gyeonggi-do (KR)

( * ) Notice: Subject to any disclaimer, the term of this patent is extended or adjusted under 35 U.S.C. 154(b) by 368 days.

(21) Appl. No.: 16/956,385

(22) PCT Filed: Dec. 18, 2018

(86) PCT No.: PCT/EP2018/085481
§ 371 (c)(1),
(2) Date: Jun. 19, 2020

(87) PCT Pub. No.: WO2019/121672
PCT Pub. Date: Jun. 27, 2019

(65) Prior Publication Data
US 2020/0361916 A1 Nov. 19, 2020

(30) Foreign Application Priority Data

Dec. 21, 2017 (EP) .................................. 17209590

(51) Int. Cl.
*H01L 51/00* (2006.01)
*C07D 405/04* (2006.01)
*C07D 405/14* (2006.01)

(52) U.S. Cl.
CPC ......... *C07D 405/14* (2013.01); *C07D 405/04* (2013.01); *H01L 51/0067* (2013.01); *H01L 51/0073* (2013.01)

(58) Field of Classification Search
CPC . C07D 405/14; C07D 405/04; H01L 51/0067; H01L 51/0073
See application file for complete search history.

(56) References Cited

U.S. PATENT DOCUMENTS

| 2018/0337341 A1 | 11/2018 | Heo et al. |
| 2018/0339967 A1 | 11/2018 | Kim et al. |
| 2019/0181351 A1 | 6/2019 | Jang et al. |

FOREIGN PATENT DOCUMENTS

| KR | 20160095667 A | 8/2016 | |
| KR | 20170116944 A | 10/2017 | |
| WO | WO 2017/135510 | * 8/2017 | ............. C09K 11/06 |

OTHER PUBLICATIONS

PCT International Search Report and Written Opinion for PCT Application No. PCT/EP2018/085481 dated Dec. 13, 2019 (11 pages).

* cited by examiner

*Primary Examiner* — Erich A Leeser
(74) *Attorney, Agent, or Firm* — Eversheds Sutherland (US) LLP

(57) ABSTRACT

The present invention relates to a triazine compound according to formula 1: suitable for use as a layer material for electronic devices, and to an organic semiconductor layer comprising at least one compound according to formula 1, as well as to an organic electronic device comprising at least one organic semiconductor layer, and a method of manufacturing the same.

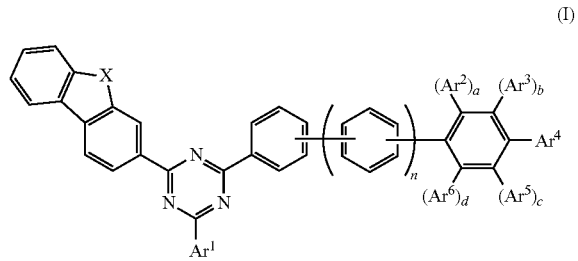

23 Claims, 2 Drawing Sheets

TRIAZINE COMPOUNDS SUBSTITUTED WITH BULKY GROUPS

CROSS REFERENCE TO RELATED APPLICATIONS

This application is a U.S. national stage application of PCT/EP2018/085481, filed Dec. 18, 2018, which claims priority to European Application No. 17209590.3, filed Dec. 21, 2017. The content of these applications is incorporated herein by reference.

TECHNICAL FIELD

The present invention relates to triazine compounds, in particular to triazine compounds substituted with bulky groups, suitable for use as a layer material for electronic devices, and relates to an organic semiconductor layer comprising at least one compound thereof, as well as to an organic electronic device comprising at least one organic semiconductor layer, and a method of manufacturing the same.

BACKGROUND ART

Organic electronic devices, such as organic light-emitting diodes OLEDs, which are self-emitting devices, have a wide viewing angle, excellent contrast, quick response, high brightness, excellent operating voltage characteristics, and color reproduction. A typical OLED comprises an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

Particularly, development of an organic material being capable of increasing electron mobility and simultaneously increasing electrochemical stability is needed so that the organic electronic device, such as an organic light emitting diode, may be applied to a large-size flat panel display.

Further, development of an organic material being capable to have an extended life span at higher current density and thereby at higher brightness is needed.

There remains a need to improve performance of organic semiconductor layers, organic semiconductor materials, as well as organic electronic devices thereof, in particular to achieve increased lifetime at higher current density and have a higher efficiency through improving the characteristics of the triazine compounds comprised therein.

There is a need for alternative organic semiconductor materials and organic semiconductor layers as well as organic electronic devices having increased lifetime at higher current density, and/or improved efficiency at low operating voltage.

In particular there is a need for alternative compounds having increased lifetime at higher current density as well as improved efficiency, and at the same time keeping the operating voltage and thereby the power consumption low to deliver long battery life for example mobile electronic devices.

DISCLOSURE

An aspect of the present invention provides a triazine compound of formula 1,

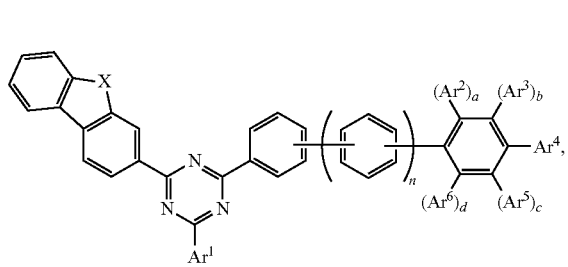

wherein

X is O, S or Se;

a, b, c, d are selected from 0 or 1, wherein $1 \leq a+b+c+d \leq 3$;

n is selected from 0, 1 or 2;

$Ar^1$ is selected from $C_1$ to $C_{16}$ alkyl, substituted or unsubstituted $C_6$ to $C_{40}$ aryl, substituted or unsubstituted $C_3$ to $C_{40}$ heteroaryl, wherein the substituents of the substituted $C_6$ to $C_{40}$ aryl and substituted $C_3$ to $C_{40}$ heteroaryl are selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, -PX($R^1$)$_2$, D, F or CN, wherein $R^1$ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;

$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl is selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN.

Hetero atoms if not otherwise stated can be individually selected from N, O, S, B, Si, P, Se, preferably from N, O and S and more preferred is N.

If not otherwise stated H can represent hydrogen or deuterium.

According to one embodiment of the triazine compound of formula 1,

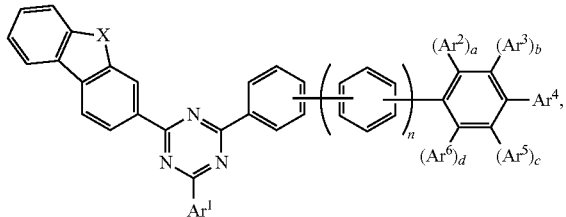

wherein
X may be O, S or Se;
a, b, c, d may be selected from 0 or 1, wherein $1 \leq a+b+c+d \leq 3$;

n may be selected from 0, 1 or 2;

$Ar^1$ may be selected from $C_1$ to $C_{16}$ alkyl, substituted or unsubstituted $C_6$ to $C_4$ aryl, substituted or unsubstituted $C_3$ to $C_{40}$ heteroaryl, wherein the substituents of the substituted $C_6$ to $C_{40}$ aryl and substituted $C_3$ to $C_{40}$ heteroaryl may be selected from H, $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, -PX($R^1$)$_2$, D, F or CN, wherein $R^1$ may be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;

$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl may be selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN;

wherein $Ar^1$ comprises at least one -PX($R^1$)$_2$ substituent.

Hetero atoms if not otherwise stated can be individually selected from N, O, S, B, Si, P, Se, preferably from N, O and S and more preferred is N.

According to one embodiment of the triazine compound of formula 1,

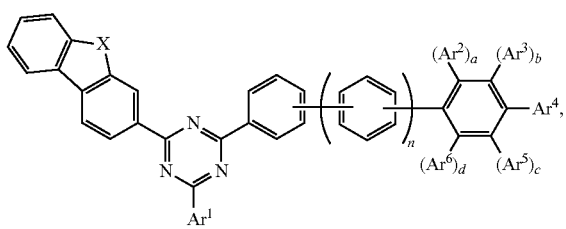

wherein
X may be O, S or Se;
a, b, c, d may be selected from 0 or 1, wherein $1 \leq a+b+c+d \leq 3$;

n may be 0;

$Ar^1$ may be selected from $C_1$ to $C_{16}$ alkyl, substituted or unsubstituted $C_6$ to $C_4$ aryl, substituted or unsubstituted $C_3$ to $C_{40}$ heteroaryl, wherein the substituents of the substituted $C_6$ to $C_{40}$ aryl and substituted $C_3$ to $C_{40}$ heteroaryl may be selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, -PX($R^1$)$_2$, D, F or CN, wherein $R^1$ may be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;

$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl may be selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN.

According to one embodiment of the triazine compound of formula 1,

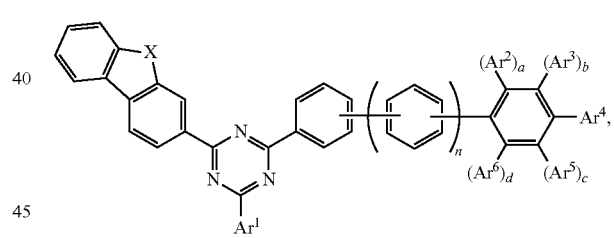

wherein
X may be O, S or Se;
a, b, c, d may be selected from 0 or 1, wherein $1 \leq a+b+c+d \leq 3$;

n may be 1;

$Ar^1$ may be selected from $C_1$ to $C_{16}$ alkyl, substituted or unsubstituted $C_6$ to $C_{40}$ aryl, substituted or unsubstituted $C_3$ to $C_{40}$ heteroaryl, wherein the substituents of the substituted $C_6$ to $C_{40}$ aryl and substituted $C_3$ to $C_{40}$ heteroaryl may be selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, -PX($R^1$)$_2$, D, F or CN, wherein $R^1$ may be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;

$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl may be selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN.

According to one embodiment of the triazine compound of formula 1,

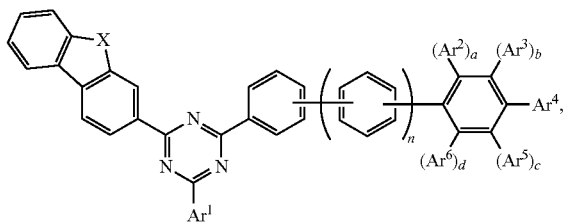

wherein

X may be O, S or Se;

a, b, c, d may be selected from 0 or 1, wherein 1≤a+b+c+d≤3;

n may be selected from 0, 1 or 2, $Ar^1$ may be selected from $C_1$ to $C_{16}$ alkyl, substituted or unsubstituted $C_6$ to $C_4$ aryl, substituted or unsubstituted $C_3$ to $C_{40}$ heteroaryl, wherein the substituents of the substituted $C_6$ to $C_{40}$ aryl and substituted $C_3$ to $C_{40}$ heteroaryl may be selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, D, F or CN;

$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl may be selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN; wherein the hetero may be individually selected from N, O, S, B, Si, P, Se, preferably from N, O and S, and more preferred is N.

According to one embodiment of the triazine compound of formula 1,

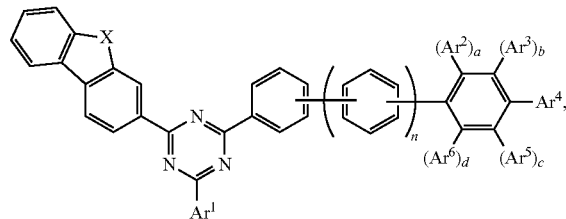

wherein

X may be O, S or Se;

a, b, c, d may be selected from 0 or 1, wherein 1≤a+b+c+d≤3;

n may be selected from 0, 1 or 2, $Ar^1$ may be selected from $C_1$ to $C_{16}$ alkyl, unsubstituted $C_6$ to $C_{40}$ aryl, unsubstituted $C_3$ to $C_{40}$ heteroaryl;

$Ar^2$, $Ar^3$, $Ar^4$, $Ar^5$ and $Ar^6$ are independently selected from unsubstituted $C_6$ to $C_{12}$ aryl or unsubstituted $C_4$ to $C_{10}$ heteroaryl; wherein the hetero atom may be individually selected from N, O, S, B, Si, P, Se, preferably from N, O and S, and more preferred is N.

According to one embodiment of the triazine compound of formula 1,

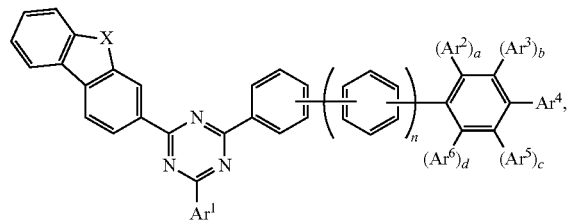

wherein

X may be O, S or Se;

a, b, c, d may be selected from 0 or 1, wherein 1≤a+b+c+d≤3;

n may be selected from 0, 1 or 2;

$Ar^1$ may be selected from substituted $C_6$ to $C_{40}$ aryl, substituted $C_3$ to $C_4$ heteroaryl, wherein the substituents of the substituted $C_6$ to $C_{40}$ aryl and substituted $C_3$ to $C_{40}$ heteroaryl may be selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, -PX($R^1$)$_2$, D, F or CN, wherein $R^1$ may be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;

$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl may be selected from $C_1$ to $C_6$ alkyl, $C_1$ to $C_6$ alkoxy, partially or perdeuterated $C_1$ to $C_6$ alkoxy, partially or perdeuterated $C_1$ to $C_6$ alkyl, partially or perfluorinated $C_1$ to $C_6$ alkyl, partially or perfluorinated $C_1$ to $C_6$ alkoxy, D, F, or CN.

According to another embodiment of the triazine compound of formula 1, wherein X may be selected from O or S.

According to another embodiment of the triazine compound of formula 1, wherein X is O.

According to another embodiment of the triazine compound of formula 1, wherein
$Ar^1$ may be selected from $C_1$ to $C_{12}$ alkyl, substituted or unsubstituted $C_6$ to $C_{24}$ aryl or substituted or unsubstituted $C_3$ to $C_{36}$ heteroaryl, wherein
the substituents of the substituted $C_6$ to $C_{24}$ aryl and substituted $C_3$ to $C_{36}$ heteroaryl may be selected from $C_1$ to $C_{12}$ alkyl, $C_1$ to $C_{12}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{12}$ alkyl, partially or perfluorinated $C_1$ to $C_{16}$ alkoxy, partially or perdeuterated $C_1$ to $C_{12}$ alkyl, partially or perdeuterated $C_1$ to $C_{16}$ alkoxy, $C_6$ to $C_{24}$ aryl, $C_3$ to $C_{25}$ heteroaryl, D, F or CN, preferably from $C_1$ to $C_{12}$ alkyl.

According to another embodiment of the triazine compound of formula 1, wherein $Ar^1$ may be selected from unsubstituted $C_6$ to $C_{24}$ aryl, preferably a $C_6$ or $C_{12}$ aryl.

According to another embodiment of the triazine compound of formula 1, wherein $Ar^1$ may be independently selected from B1 to B77, wherein a) B1 to B6 are substituted or unsubstituted non-heteroaryl groups:

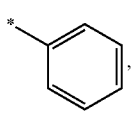

B1

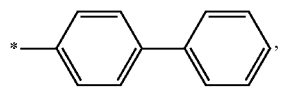

B2

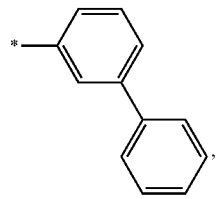

B3

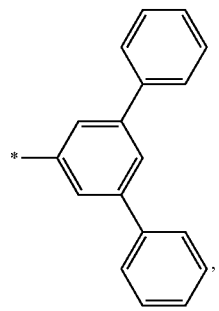

B4

-continued

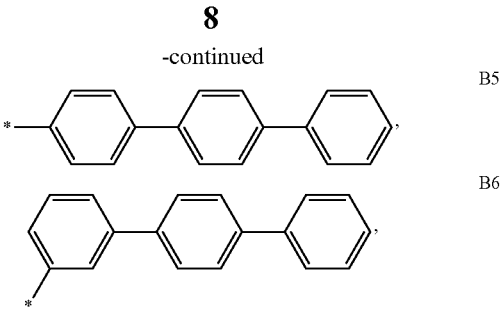

B5

B6 or b) B7 to B23 are substituted or unsubstituted annelated non-heteroaryl groups:

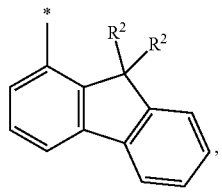

B7

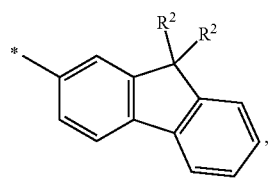

B8

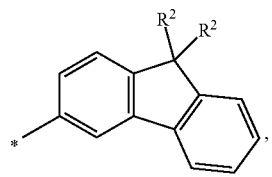

B9

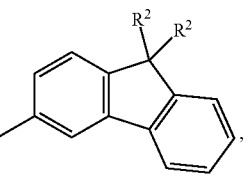

B10

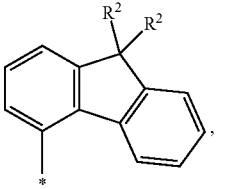

B11

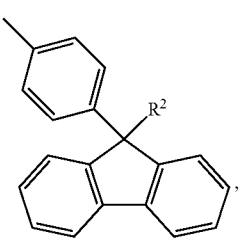

B12

B13 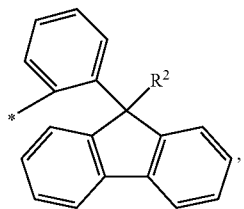
B14 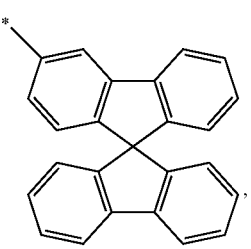
B15 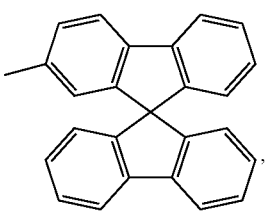
B16 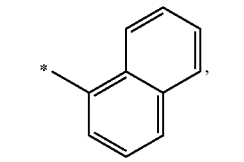
B17 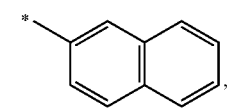
B18 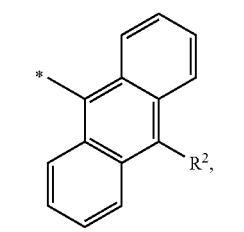
B19 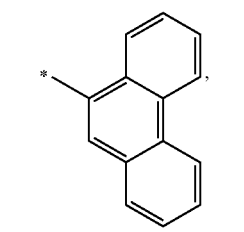
B20 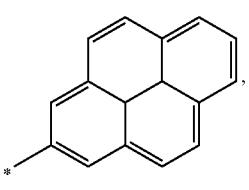
B21 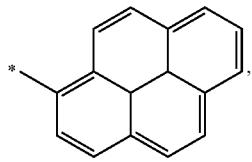
B22 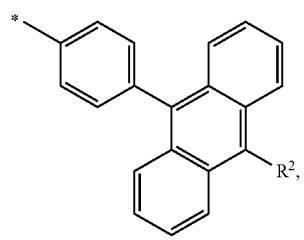
B23 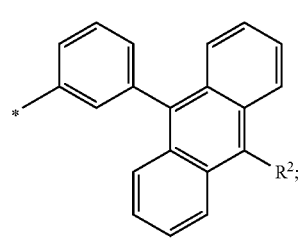
or
c) B24 to B31 are dibenzofurane/dibenzothiophene group:
or
B24 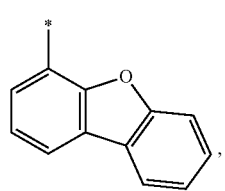
B25 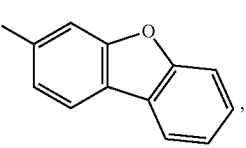
B26 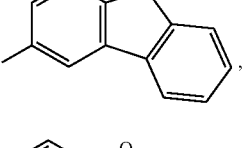
B27 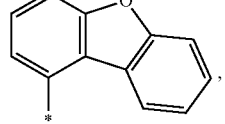

-continued
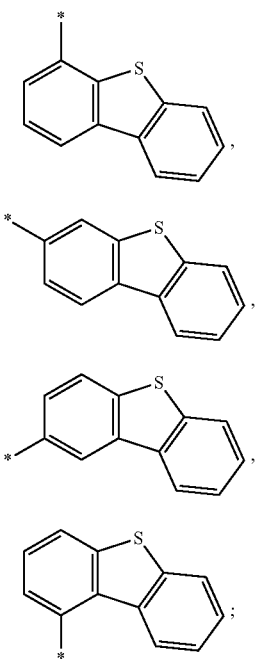
B28,
B29,
B30,
B31;
or
d) B32 to B34 are unsubstituted pyridine groups:
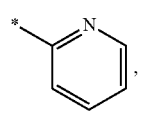 B32,
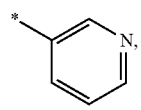 B33,
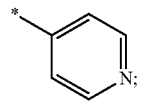 B34;
or
e) B35 to B62 are unsubstituted or substituted heteroarylene groups:
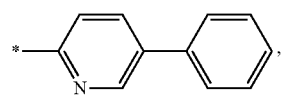 B35,
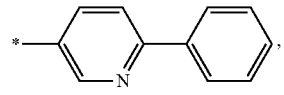 B36,
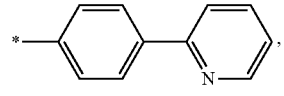 B37,
-continued
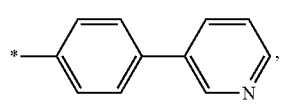 B38,
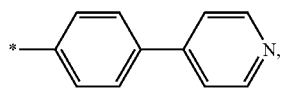 B39,
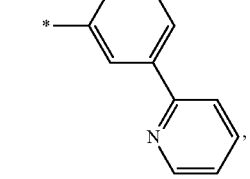 B40,
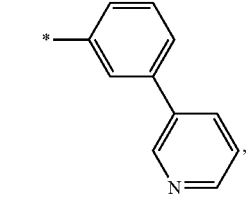 B41,
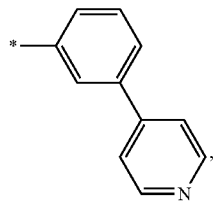 B42,
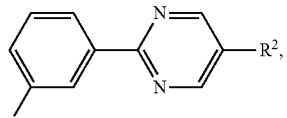 B43,
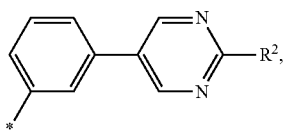 B44,
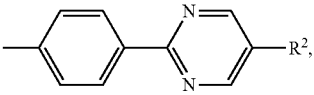 B45,
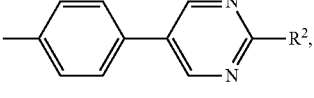 B46,
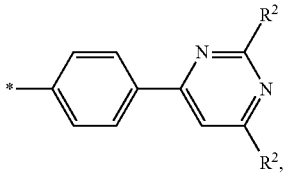 B47,

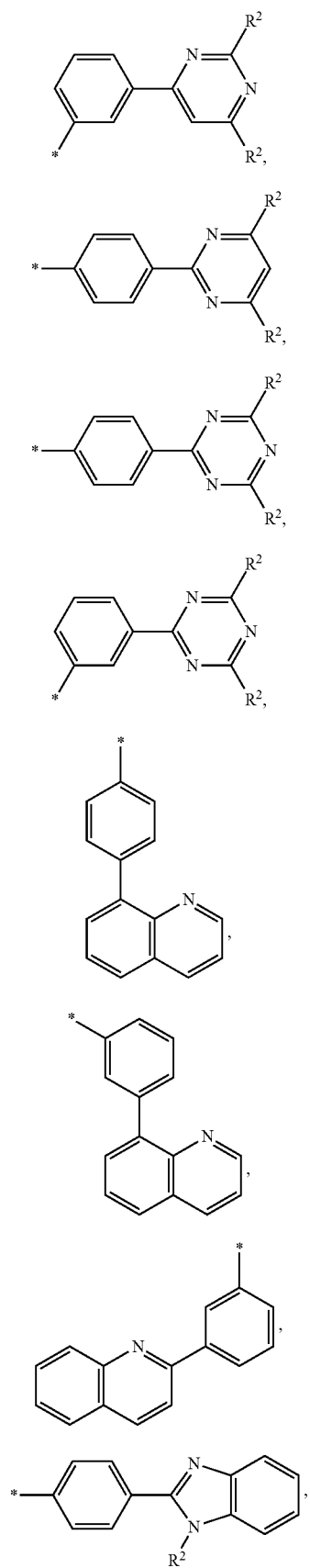
B48
B49
B50
B51
B52
B53
B54
B55
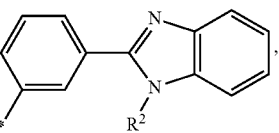 B56
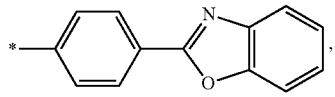 B57
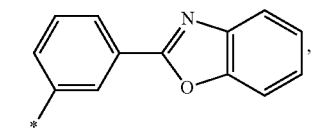 B58
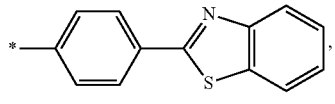 B59
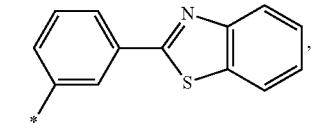 B60
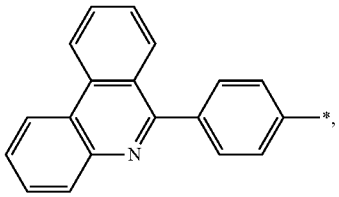 B61
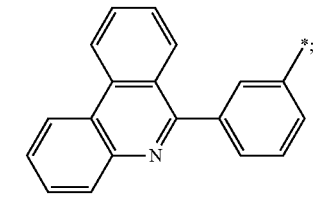 B62
or
f) B63 to B65 unsubstituted annelated hetero arylene groups:
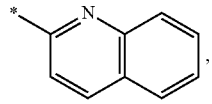 B63
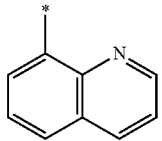 B64

-continued

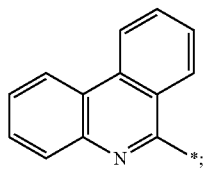
B65 or
g) B66 and B67 are nitrile substituted phenyl groups

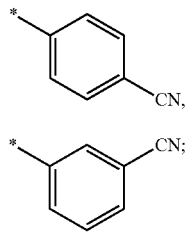
B66

B67 or
h) B68 to B70 are nitrile substituted biphenyl groups

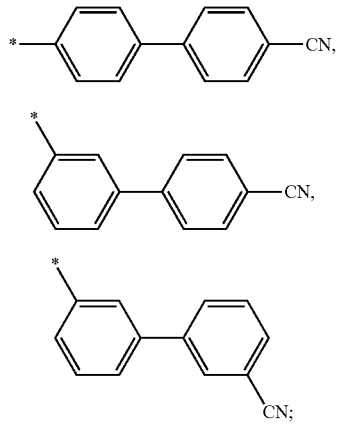
B68

B69

B70 or
i) B71 to B77 are carbazole groups

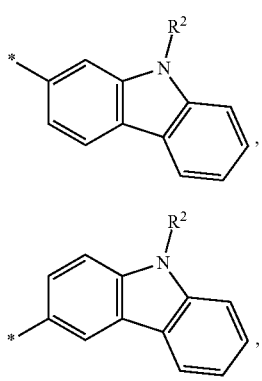
B71

B72

-continued

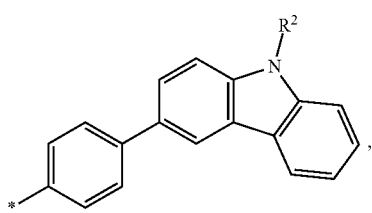
B73

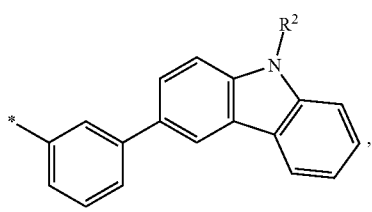
B74

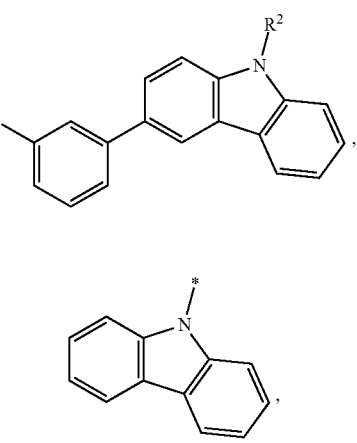
B75

B76

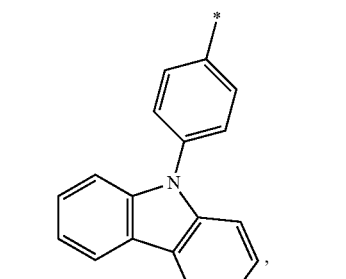

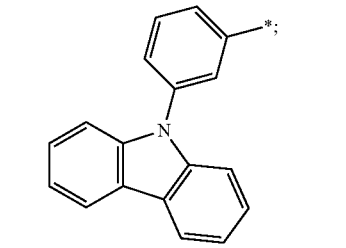
B77 wherein
the substituent $R^2$ may be independently selected from H, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, $C_6$ to $C_{24}$ aryl and $C_3$ to $C_{25}$ heteroaryl.

In another embodiment, $Ar^1$ may be selected from B1 to B6 and B16 to B23, preferably from B1 to B6, B16 to B17 and B19.

According to another embodiment of the triazine compound of formula 1, wherein $Ar^1$ may be independently selected from structures C1 to C5:

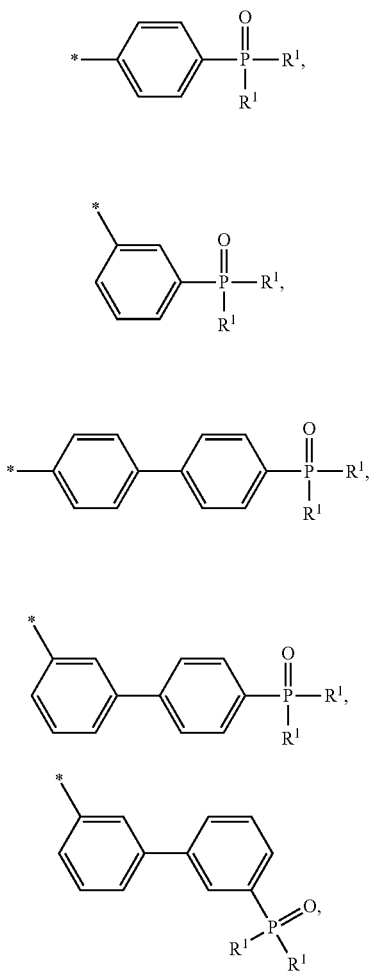

wherein

R¹ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl.

Preferably, R¹ may be independently selected from $C_1$ to $C_8$ alkyl, $C_1$ to $C_8$ alkoxy, partially or perfluorinated $C_1$ to $C_8$ alkyl, partially or perfluorinated $C_1$ to $C_8$ alkoxy, partially or perdeuterated $C_1$ to $C_8$ alkyl, partially or perdeuterated $C_1$ to $C_8$ alkoxy, $C_6$ to $C_{12}$ aryl, $C_3$ to $C_{20}$ heteroaryl.

Further preferred, R¹ may be independently selected from $C_1$ to $C_8$ alkyl, partially or perdeuterated $C_1$ to $C_8$ alkyl, partially or perdeuterated $C_1$ to C alkoxy, $C_6$ to $C_{12}$ aryl, $C_3$ to $C_{20}$ heteroaryl.

More preferred, R¹ may be phenyl or $C_1$ to $C_4$ alkyl, even more preferred phenyl or methyl.

According to another embodiment of the triazine compound of formula 1, wherein at least one to at most three substituents of $Ar^2$, $Ar^3$, $Ar^5$ and $Ar^6$ are independently selected from unsubstituted $C_6$ to $C_{12}$ aryl or unsubstituted $C_4$ to $C_{10}$ heteroaryl.

According to another embodiment of the triazine compound of formula 1, wherein at least one to at most three substituents of $Ar^2$, $Ar^3$, $Ar^5$ and $Ar^6$ are independently selected from unsubstituted $C_6$ to $C_{12}$ aryl.

According to another embodiment of the triazine compound of formula 1, wherein at least one to at most three substituents of $Ar^2$, $Ar^3$, $Ar^5$ and $Ar^6$ are independently selected from phenyl, biphenyl, naphthyl, pyridyl, quinolinyl, quinazolinyl; preferably at least one $Ar^2$, $Ar^3$, $Ar^5$ and $Ar^6$ may be selected from phenyl; more preferably at least two $Ar^2$, $Ar^3$, $Ar^5$ and $Ar^6$ may be selected from phenyl; also preferred at least three of $Ar^2$, $Ar^3$, $Ar^5$ and $Ar^6$ may be selected from phenyl.

According to another embodiment of the triazine compound of formula 1, wherein at least one to at most three substituents of $Ar^2$, $Ar^3$, $Ar^5$ and $Ar^6$ are independently selected from phenyl, biphenyl, naphthyl, pyridyl, quinolinyl, quinazolinyl.

According to another embodiment of the triazine compound of formula 1, wherein at least one to at most three substituents of $Ar^2$, $Ar^3$, $Ar^5$ and $Ar^6$ are independently selected from phenyl.

According to another embodiment of the triazine compound of formula 1, wherein two or three of Ar2, Ar3, Ar5, Ar6 may be selected from phenyl.

According to another embodiment of the triazine compound of formula 1, wherein $Ar^4$ may be selected from unsubstituted $C_6$ to $C_{12}$ aryl or unsubstituted $C_4$ to $C_{10}$ heteroaryl.

According to another embodiment of the triazine compound of formula 1, wherein $Ar^4$ may be selected from unsubstituted $C_6$ to $C_{12}$ aryl.

According to another embodiment of the triazine compound of formula 1, wherein $Ar^4$ may be selected from phenyl, biphenyl, naphthyl, pyridyl, quinolinyl, quinazolinyl.

According to another embodiment of the triazine compound of formula 1, wherein $Ar^4$ may be phenyl.

According to another embodiment of the triazine compound of formula 1, wherein three of $Ar^2$, $Ar^3$, $Ar^5$, $Ar^6$ and in addition $Ar^4$ may be selected from phenyl.

According to another embodiment of the triazine compound of formula 1, wherein n=0 or 1, preferably n=0. According to another embodiment of the triazine compound of formula 1, wherein n=0. According to another embodiment of the triazine compound of formula 1, wherein n=1. According to another embodiment of the triazine compound of formula 1, wherein n=2.

According to another embodiment of the triazine compound of formula 1, wherein a=1, b=0, c=0 and d=1; or a=0, b=0, c=0 and d=1; or a=0, b=0, c=1 and d=1; or a=0, b=1, c=1 and d=0; or a=1, b=1, c=1 and d=0.

According to another embodiment of the triazine compound of formula 1, wherein a=1, b=0, c=0 and d=1. According to another embodiment of the triazine compound of formula 1, wherein a=0, b=0, c=0 and d=1. According to another embodiment of the triazine compound of formula 1, wherein a=0, b=0, c=1 and d=1. According to another embodiment of the triazine compound of formula 1, wherein a=1, b=1, c=1 and d=0.

According to another embodiment of the triazine compound of formula 1, the triazine compound may be selected from D1 to D9:

D1
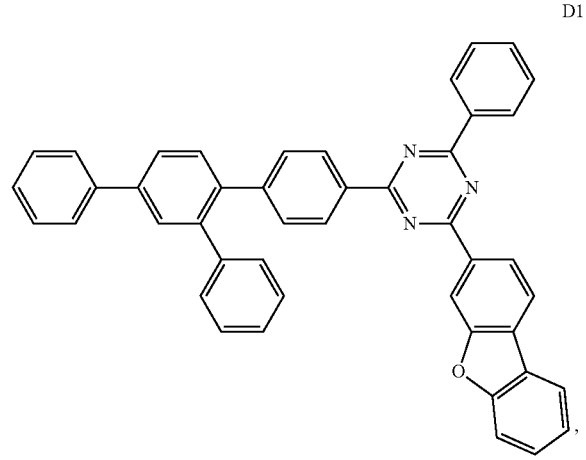
D2
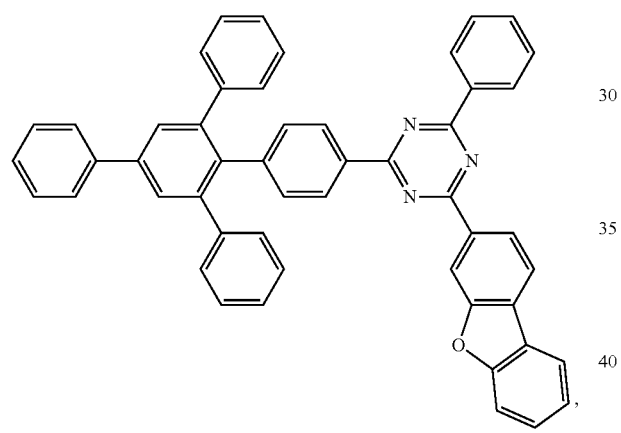
D3
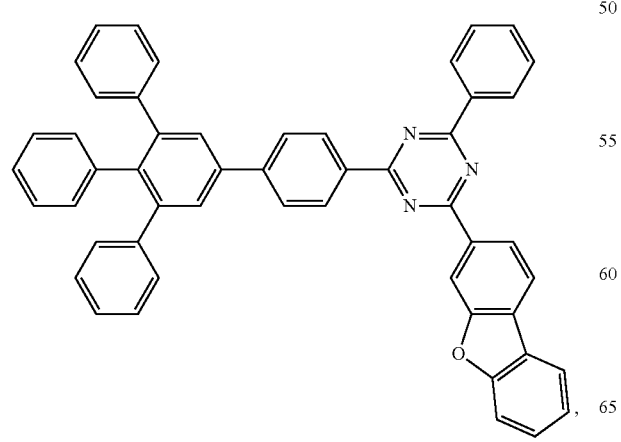
D4
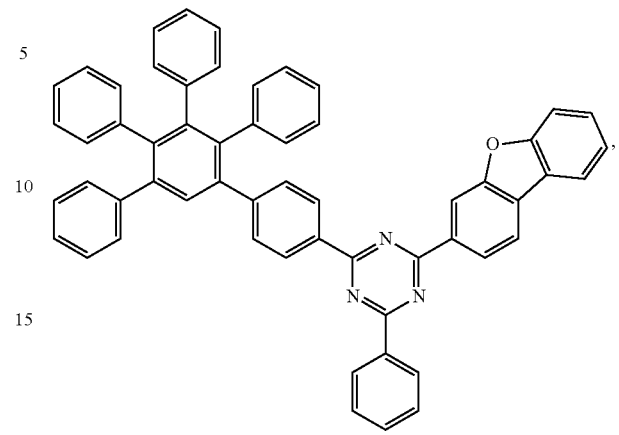
D5
D6
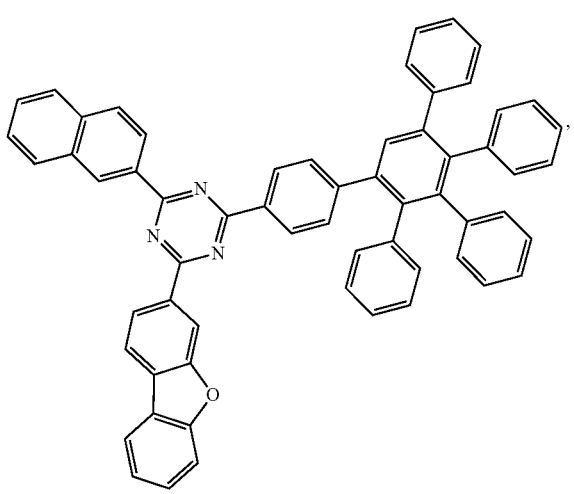

-continued

D7
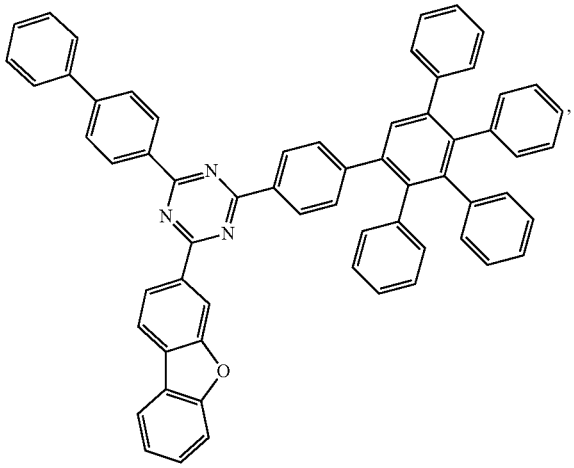

D8
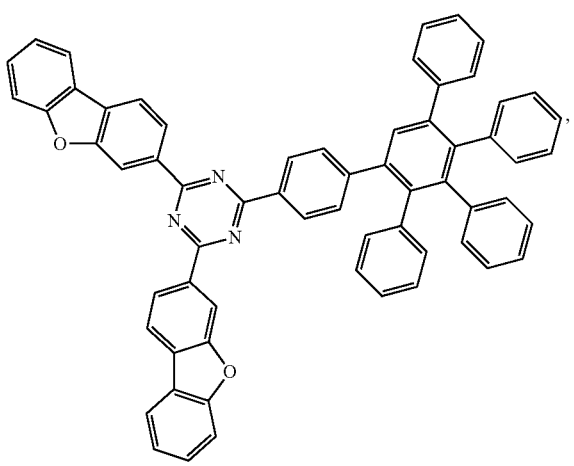

D9
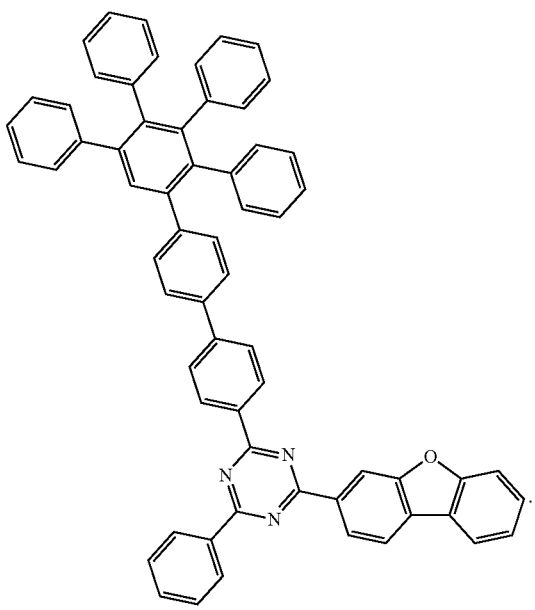

According to an aspect the triazine compound of formula 1 can be used as a matrix material for a dopant material.

According to an aspect the layer material can be an organic semiconductor layer, which is used for an organic electronic device. For example, the organic electronic device can be an OLED or there like.

The triazine compounds represented by formula 1 have strong electron transport characteristics to increase charge mobility and/or stability and thereby to improve luminance efficiency, voltage characteristics, and/or lifetime characteristics.

The triazine compounds represented by formula 1 have high electron mobility and a low operating voltage.

The triazine compounds represented by formula 1 and an organic semiconductor layer consisting or comprising of triazine compound of formula 1 may be non-emissive.

In the context of the present specification the term "essentially non-emissive" or "non-emitting" means that the contribution of the triazine compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconductor layer comprising the triazine compound of formula 1 is essentially non-emissive or non-emitting.

The term "free of", "does not contain", "does not comprise" does not exclude impurities which may be present in the triazine compounds prior to deposition. Impurities have no technical effect with respect to the object achieved by the present invention.

The operating voltage, also named U, is measured in Volt (V) at 10 milliAmpere per square centimeter (mA/cm2).

The candela per Ampere efficiency, also named cd/A efficiency, is measured in candela per ampere at 10 milliAmpere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The rate onset temperature is measured in ° C. and describes the VTE source temperature at which measurable evaporation of a compound commences at a pressure of less than $10^{-5}$ mbar.

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

As used herein, "weight percent", "wt.-%", "percent by weight", "% by weight", and variations thereof refer to a composition, component, substance or agent as the weight of that composition, component, substance or agent of the respective electron transport layer divided by the total weight of the composition thereof and multiplied by 100. It is understood that the total weight percent amount of all components, substances or agents of the respective electron transport layer are selected such that it does not exceed 100 wt.-%.

As used herein, "volume percent", "vol.-%", "percent by volume", "% by volume", and variations thereof refer to an elemental metal, a composition, component, substance or agent as the volume of that elemental metal, component, substance or agent of the respective electron transport layer divided by the total volume of the respective electron transport layer thereof and multiplied by 100. It is understood that the total volume percent amount of all elemental metal, components, substances or agents of the respective cathode electrode layer are selected such that it does not exceed 100 vol.-%.

All numeric values are herein assumed to be modified by the term "about", whether or not explicitly indicated. As used herein, the term "about" refers to variation in the numerical quantity that can occur.

Whether or not modified by the term, "about", the claims include equivalents to the quantities.

It should be noted that, as used in this specification and the appended claims, the singular forms, "a", "an", and, "the" include plural referents unless the content clearly dictates otherwise.

It should be noted that, as used in this specification and the appended claims, "*" if not otherwise defined indicates the chemical bonding position.

The anode electrode and cathode electrode may be described as anode electrode/cathode electrode or anode electrode/cathode electrode or anode electrode layer/cathode electrode layer.

According to another aspect, an organic optoelectronic device comprises an anode layer and a cathode layer facing each other and at least one organic semiconductor layer between the anode layer and the cathode layer, wherein the organic semiconductor layer comprises or consists of the triazine compound of formula 1.

According to yet another aspect, a display device comprising the organic electronic device, which can be an organic optoelectronic device, is provided.

In the present specification, when a definition is not otherwise provided, an "alkyl group" may refer to an aliphatic hydrocarbon group. The alkyl group may refer to "a saturated alkyl group" without any double bond or triple bond. The alkyl group may be a linear, cyclic or branched alkyl group.

The term "alkyl group" includes $C_1$ to $C_{16}$ alkyl, $C_3$ to $C_{16}$ branched alkyl, and $C_3$ to $C_{16}$ cyclic alkyl.

The alkyl group may be a $C_1$ to $C_{16}$ alkyl group, or preferably a $C_1$ to $C_{12}$ alkyl group. More specifically, the alkyl group may be a $C_1$ to $C_{14}$ alkyl group, or preferably a $C_1$ to $C_{10}$ alkyl group or a $C_1$ to $C_6$ alkyl group. For example, a $C_1$ to $C_4$ alkyl group comprises 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, a cyclohexyl group, and the like.

In the present specification $R^1$ of $-PX(R^1)_2$ can be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl, that means that both substutents of $R^1$ can be same or different selected, preferably both $R^1$ of $-PX(R^1)_2$ are selected the same.

In the present specification "arylene group" may refer to a group comprising at least one hydrocarbon aromatic moiety, and all the elements of the hydrocarbon aromatic moiety may have p-orbitals which form conjugation, for example a phenyl group, a naphthyl group, an anthracenyl group, a phenanthrenyl group, a pyrenyl group, a fluorenyl group and the like.

The term "heteroarylene" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S.

A heteroarylene ring may comprise at least 1 to 3 heteroatoms. Preferably a heteroarylene ring may comprise at least 1 to 3 heteroatoms individually selected from N, S and/or O.

Further preferred in addition to the triazine group of formula 1 at least one additional heteroaryl/ene ring may comprise at least 1 to 3 N-atoms, or at least 1 to 2-N atoms or at least one N-atom.

According to another preferred embodiment the triazine compound according to formula 1 may comprise:
  at least 6 to 25 aromatic rings, preferably at least 7 to 22 aromatic rings, further preferred at least 8 to 20 aromatic rings, in addition preferred at least 9 to 15 aromatic rings and more preferred at least 10 to 14 aromatic rings; wherein
  at least 2 to 5, preferably 3 to 4 or 2 to 3, are heteroaromatic rings.

According to one embodiment the triazine compound according to formula 1:
  comprises at least about 6 to about 20 aromatic rings, preferably at least about 7 to about 18 aromatic rings, further preferred at least about 9 to about 16 aromatic rings, in addition preferred at least about 10 to about 15 aromatic rings and more preferred at least about 11 to about 14 aromatic rings; and/or
  the triazine compound of formula 1 comprises at least about 2 to about 6, preferably about 3 to about 5 or about 2 to about 4, hetero aromatic rings, wherein the hetero atoms can be selected from N, O, S and/or
  comprises at least one fluorene ring and at least one hetero-fluorene ring, wherein the hetero atoms can be selected from N, O, S; and/or
  comprises at least one triazine ring, or at least two triazine rings.

According to a further preferred embodiment the triazine compound of formula 1 comprises at least 2 to 7, preferably 2 to 5, or 2 to 3 hetero aromatic rings.

According to a further preferred embodiment the triazine compound of formula 1 comprises at least 2 to 7, preferably 2 to 5, or 2 to 3 hetero aromatic rings, wherein at least one of the aromatic rings is a five member hetero aromatic ring.

According to a further preferred embodiment the triazine compound of formula 1 comprises at least 3 to 7, preferably 3 to 6, or 3 to 5 hetero aromatic rings, wherein at least two of the hetero aromatic rings are five member hetero-aromatic-rings.

According to one embodiment the triazine compound according to formula 1 may comprise at least 6 to 12 non-hetero aromatic rings and 2 to 3 hetero aromatic rings.

According to one preferred embodiment the triazine compound according to formula 1 may comprise at least 7 to 12 non-hetero aromatic rings and 2 to 5 hetero aromatic rings.

According to one preferred embodiment the triazine compound according to formula 1 may comprise at least 7 to 11 non-hetero aromatic rings and 2 to 3 hetero aromatic rings.

According to another embodiment of formula 1, wherein for Ar², Ar³, Ar⁴, Ar⁵ and/or Ar⁶ at least one heteroarylene group is selected from pyridinyl, quinolinyl or quinazolinyl.

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 µL Mettler Toledo aluminum pan with lid, a<1 mm hole is pierced into the lid).

According to another embodiment the triazine compound of formula 1 may have a melting point of about ≥250° C. and about ≤380° C., preferably about ≥260° C. and about ≤370° C., further preferred about ≥270° C. and about ≤360° C., in addition preferred about ≥280° C. and about ≤350° C., also preferred about ≥290° C. and about ≤340° C. and likewise preferred about ≥300° C. and about ≤330° C.

Glass Transition Temperature

The glass transition temperature is measured under nitrogen and using a heating rate of 10 K per min in a Mettler Toledo DSC 822e differential scanning calorimeter as described in DIN EN ISO 11357, published in March 2010.

According to another embodiment the triazine compound of formula 1 may have a glass transition temperature Tg of about ≥115° C. and about ≤380° C., preferably about ≥120° C. and about ≤350° C., further preferred about ≥120° C. and about ≤320° C., in addition preferred about ≥120° C. and about ≤200° C. and also preferred about ≥125° C. and about ≤180° C.

According to another embodiment the triazine compound of formula 1 may have a glass transition temperature Tg of about ≥120° C. and about ≤200° C.

Rate Onset Temperature

The rate onset temperature is determined by loading 100 mg compound into a VTE source. The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Ångstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200 to 255° C. If the rate onset temperature is below 200° C. the evaporation may be too rapid and therefore difficult to control. If the rate onset temperature is above 255° C. the evaporation rate may be too low which may result in low takt time and decomposition of the organic compound in VTE source may occur due to prolonged exposure to elevated temperatures.

The rate onset temperature is an indirect measure of the volatility of a compound. The higher the rate onset temperature the lower is the volatility of a compound.

According to another embodiment the triazine compound of formula 1 may have a rate onset temperature $T_{RO}$ of about ≥200° C. and about ≤350° C., preferably about ≥220° C. and about ≤350° C., further preferred about ≥240° C. and about ≤320° C., in addition preferred about ≥240° C. and about ≤300° C.

Dipole Moment

The dipole moment $|\vec{\mu}|$ of a molecule containing N atoms is given by:

$$\vec{\mu} = \sum_{i}^{N} q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method. The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

According to one embodiment the triazine compounds according to formula 1 may have a dipole moment (Debye) in the range from about ≥0.4 to about ≤1.50, preferably from about ≥0.45 to about ≤1.45.

Calculated HOMO and LUMO

The HOMO and LUMO are calculated with the program package TURBOMOLE V6.5. The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

According to one embodiment the triazine compounds according to formula 1 may have a LUMO energy level (eV) in the range from about −2.00 eV to about −1.90 eV, preferably from about −1.99 eV to about −1.91 eV, further preferred from about −1.98 eV to about −1.92 eV, also preferred from about −1.97 eV to about −1.93 eV, in addition preferred from about −1.96 eV to about −1.94 eV, or about 1.95 eV.

Technical Effect

Surprisingly, it was found that the triazine compounds of formula 1 and the inventive organic electronic devices solve the problem underlying the present invention by being superior over the organic electroluminescent devices and compounds known in the art, in particular with respect to cd/A efficiency, also referred to as current efficiency and to lifetime. At the same time the operating voltage is kept at a similar or even improved level which is important for reducing power consumption and increasing battery life, for example of a mobile display device. High cd/A efficiency is important for high efficiency and thereby increased battery life of a mobile device, for example a mobile display device. Long lifetime at high current density is important for the longevity of a device which is run at high brightness.

It was additional surprisingly found that the calculated LUMO level of triazine compounds of formula 1 is significantly more negative than the LUMO of the state of the art.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned property of cd/A efficiency and/or lifetime. These compounds are discussed herein to be particularly preferred.

Further an organic optoelectronic device having high efficiency and/or long lifetime may be realized.

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm, and non-transparent metal anodes may have a thickness from about 15 nm to about 150 nm.

Hole Injection Layer (HIL)

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region comprises a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

The hole injection layer may further comprise a p-dopant to improve conductivity and/or hole injection from the anode.

p-Dopant

In another aspect, the p-dopant may be homogeneously dispersed in the hole injection layer.

In another aspect, the p-dopant may be present in the hole injection layer in a higher concentration closer to the anode and in a lower concentration closer to the cathode.

The p-dopant may be one of a quinone derivative or a radialene compound but not limited thereto. Non-limiting examples of the p-dopant are quinone derivatives such as tetracyanoquinonedimethane (TCNQ), 2,3,5,6-tetrafluorotetracyano-1,4-benzoquinonedimethane (F4-TCNQ), 4,4',4"-((1E,1'E,1"E)-cyclopropane-1,2,3-triylidenetris(cyanomethanylylidene))-tris(2,3,5,6-tetrafluorobenzonitrile).

According to another embodiment, the device comprising a triazine compound of formula 1 may further comprise a layer comprising a radialene compound and/or a quinodimethane compound.

In another embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have formula (XX) and/or the quinodimethane compound may have formula (XXIa) or (XXIv):

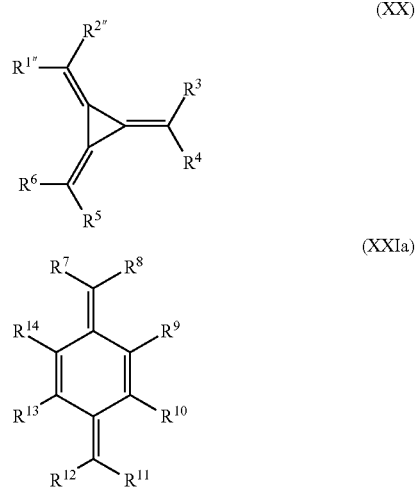

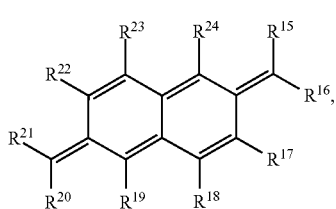

(XXIb)

wherein $R^{1\prime\prime}$, $R^{2\prime\prime}$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from an electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and electron withdrawing groups. Electron withdrawing group that can be suitable used are above mentioned.

Hole Transport Layer (HTL)

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region comprises the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in operating voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triarylene amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency.

Emission Layer (EML)

The emission layer may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

A thickness of the emission layer may be about 100 Å to about 1000 Å, for example about 200 Å to about 600 Å. When the thickness of the emission layer is within these ranges, the emission layer may have improved emission characteristics without a substantial increase in operating voltage.

Emitter Host

According to another embodiment, the emission layer comprises compound of formula 1 as emitter host.

The emitter host compound has at least three aromatic rings, which are independently selected from carbocyclic rings and heterocyclic rings.

Other compounds that can be used as the emitter host is an anthracene matrix compound represented by formula 400 below:

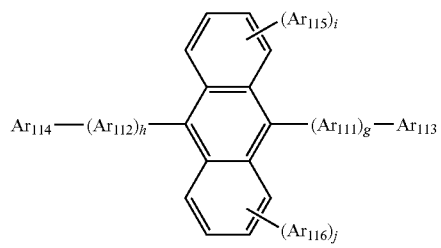

Formula 400

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ arylene group; and g, h, i, and j may be each independently an integer from 0 to 4.

In some embodiments, $Ar_{111}$ and $Ar_{112}$ in formula 400 may be each independently one of a phenylene group, a naphthalene group, a phenanthrenylene group, or a pyrenylene group; or
a phenylene group, a naphthalene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of
  a $C_1$-$C_{10}$ alkyl group substituted with at least one of a phenyl group, a naphthyl group, or an anthryl group;
  a phenyl group, a naphthyl group, an anthryl group, a pyrenyl group, a phenanthrenyl group, or a fluorenyl group;
  a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group

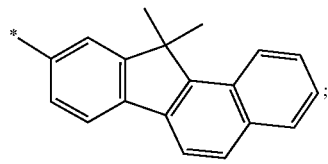 [SMILES: *c1ccc2c(c1)C(C)(C)c1c-2ccc2ccccc12]

or formulas 7 or 8

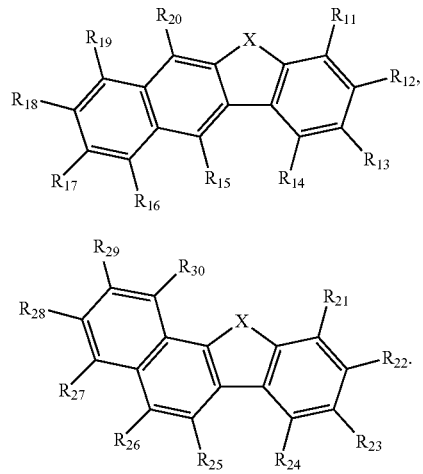

Wherein in the formulas 7 and 8, X is selected form an oxygen atom and a sulfur atom, but embodiments of the invention are not limited thereto.

In the formula 7, any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula 8, any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

Emitter Dopant

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emitter may be a red, green, or blue emitter.

The dopant may be a fluorescent dopant, for example ter-fluorene, the structures are shown below. 4.4'-bis(4-diphenyl amiostyryl)biphenyl (DPAVBI, 2,5,8,11-tetra-tert-butyl perylene (TBPe), and Compound 8 below are examples of fluorescent blue dopants.

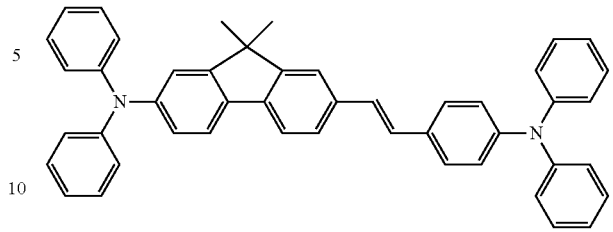

Compound 8

The dopant may be a phosphorescent dopant, and examples of the phosphorescent dopant may be an organic metal compound comprising Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$$J_2MX(Z).$$

In formula Z, M is a metal, and J and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the J and X may be, for example a bidendate ligand.

One or more emission layers may be arranged between the anode and the cathode. To increase overall performance, two or more emission layers may be present.

Charge Generation Layer

A charge generation layer (also named CGL) may be arranged between the first and the second emission layer, and second and third emission layer, if present. Typically, the CGL comprises a n-type charge generation layer (also named n-CGL or electron generation layer) and a p-type charge generation layer (also named p-CGL or hole generation layer). An interlayer may be arranged between the n-type CGL and the p-type CGL.

In one aspect, the n-type CGL may comprise a triazine compound of formula 1. The n-type CGL further comprises a metal, metal salt or organic metal complex, preferably a metal. The metal may be selected from an alkali, alkaline earth or rare earth metal.

The p-type CGL may comprise a dipyrazino[2,3-f:2',3'-h]quinoxaline, a quinone compound or a radialene compound, preferably dipyrazino[2,3-f:2',3'-h]quinoxaline-2,3,6,7,10,11-hexacarbonitrile or a compound or formula (XX) and/or a compound of formula (XXIa) or (XXIb).

In another aspect, the n-type and p-type CGL are in direct contact.

Electron Transport Layer (ETL)

According to another embodiment, the organic semiconductor layer that comprises triazine compound of formula 1 is an electron transport layer. In another embodiment the electron transport layer may consist of triazine compound of formula 1.

For example, an organic light emitting diode according to an embodiment of the present invention comprises at least one electron transport layer, and in this case, the electron transport layer comprises triazine compound of formula 1, or preferably of at least one compound of formulae D1 to D9.

In another embodiment, the organic electronic device comprises an electron transport region of a stack of organic layers formed by two or more electron transport layers, wherein at least one electron transport layer comprises triazine compound of formula 1.

The electron transport layer may include one or two or more different electron transport compounds.

According to another embodiment, a second electron transport layer comprises at least one compound of formula 1 according to the invention and a first electron transport layer comprises a matrix compound, which is selected different to the triazine compound of formula 1 according to the invention, and may be selected from:
- an anthracene based compound or a hetero substituted anthracene based compound, preferably 2-(4-(9,10-di(naphthalen-2-yl)anthracene-2-yl)phenyl)-1-phenyl-1H-benzo[d]imidazole and/or N4,N4"-di(naphthalen-1-yl)-N4,N4"-diphenyl-[1,1':4',1"-terphenyl]-4,4"-diamine.

According to another embodiment, a first electron transport layer comprises at least one compound of formula 1 according to the invention and a second electron transport layer comprises a matrix compound, which is selected different to the triazine compound of formula 1 according to the invention, and may be selected from:
- a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide; or
- a substituted phenanthroline compound, preferably 2,4,7,9-tetraphenyl-1,10-phenanthroline or 2,9-di(biphenyl-4-yl)-4,7-diphenyl-1,10-phenanthroline.

According to another embodiment a first electron transport layer comprises at least one compound of formula 1 according to the invention and a second electron transport layer comprises a matrix compound, which is selected different to the triazine compound of formula 1 according to the invention, and may be selected from a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide.

According to another embodiment, a first and a second electron transport layers comprise triazine compound of formula 1, wherein the triazine compound of formula 1 is not selected the same.

The thickness of the first electron transport layer may be from about 0.5 nm to about 100 nm, for example about 2 nm to about 40 nm. When the thickness of the first electron transport layer is within these ranges, the first electron transport layer may have improved electron transport ability without a substantial increase in operating voltage.

A thickness of an optional second electron transport layer may be about 1 nm to about 100 nm, for example about 2 nm to about 20 nm. When the thickness of the electron transport layer is within these ranges, the electron transport layer may have satisfactory electron transporting ability without a substantial increase in operating voltage.

The electron transport layer may further comprise a monovalent or divalent metal halide or an organic monovalent or divalent metal complex, preferably an alkali halide and/or alkali organic complex.

According to another embodiment, the first and second electron transport layers comprise triazine compound of formula 1, wherein the second electron transport layer further comprises an alkali halide and/or alkali organic complex.

Alkali Halide

Alkali halides, also known as alkali metal halides, are the family of inorganic compounds with the chemical formula MX, where M is an alkali metal and X is a halogen.

M can be selected from Li, Na, Potassium, Rubidium and Cesium.

X can be selected from F, Cl, Br and J.

According to various embodiments of the present invention a lithium halide may be preferred. The lithium halide can be selected from the group comprising LiF, LiCl, LiBr and LiJ. However, most preferred is LiF.

The alkali halide is essentially non-emissive or non-emissive.

Alkali Organic Complex

The alkali organic complex comprises an alkali metal and at least one organic ligand. The alkali metal is preferably selected from lithium.

According to various embodiments of the present invention the organic ligand of the lithium organic complex is a quinolate, a borate, a phenolate, a pyridinolate or a Schiff base ligand;
- preferably the lithium quinolate complex has the formula III, IV or V:

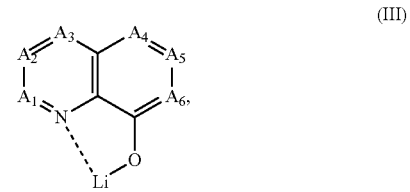

(III)

(IV)

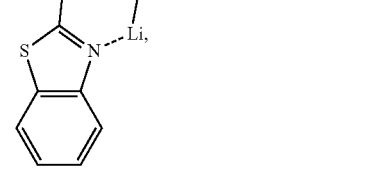

(V)

wherein
- $A_1$ to $A_6$ are same or independently selected from CH, CR, N and O;
- R is same or independently selected from hydrogen, halogen, alkyl or arylene or heteroarylene with 1 to 20 carbon atoms; and more preferred A1 to A6 are CH;
- preferably the borate based organic ligand is a tetra(1H-pyrazol-1-yl)borate;
- preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;
- preferably the pyridinolate is a 2-(diphenylphosphoryl)pyridin-3-olate.

According to various embodiments of the present invention the organic ligand of the alkali organic complex, preferably of a lithium organic complex, can be a quinolate. Quinolates that can be suitable used are disclosed in WO 2013079217 A1 and incorporated by reference.

According to various embodiments of the present invention the organic ligand of the lithium organic complex can be a borate based organic ligand, Preferably the lithium organic complex is a lithium tetra(1H-pyrazol-1-yl)borate. Borate based organic ligands that can be suitable used are disclosed in WO 2013079676 A1 and incorporated by reference.

According to various embodiments of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group of pyridinolate, preferably 2-(diphenylphosphoryl)pyridin-3-olate. Pyridine phenolate ligands that can be suitable used are disclosed in JP 2008195623 and incorporated by reference.

In addition, phenolate ligands can be selected from the group of imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group of oxazol phenolates, preferably 2-(benzo[d]oxazol-2-yl)phenolate. Oxazol phenolate ligands that can be suitable used are disclosed in US 20030165711 and incorporated by reference.

The alkali organic complex may be essentially non-emissive.

Electron Injection Layer (EIL)

According to another aspect of the invention, the organic electroluminescent device may further comprise an electron injection layer between the electron transport layer (first-ETL) and the cathode.

The electron injection layer (EIL) may facilitate injection of electrons from the cathode.

According to another aspect of the invention, the electron injection layer comprises:
(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or
(ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in operating voltage.

The electron injection layer may comprise a triazine compound of formula 1.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), silver (Ag) etc. In order to manufacture a top-emission light-emitting device having a reflective anode deposited on a substrate, the cathode may be formed as a light-transmissive electrode from, for example, indium tin oxide (ITO), indium zinc oxide (IZO) or silver (Ag).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

Substrate

A substrate may be further disposed under the anode or on the cathode. The substrate may be a substrate that is used in a general organic light emitting diode and may be a glass substrate or a transparent plastic substrate with strong mechanical strength, thermal stability, transparency, surface smoothness, ease of handling, and water resistance.

Hereinafter, the embodiments are illustrated in more detail with reference to examples. However, the present disclosure is not limited to the following examples.

DESCRIPTION OF THE DRAWINGS

These and/or other aspects and advantages of the present invention will become apparent and more readily appreciated from the following description of the exemplary embodiments, taken in conjunction with the accompanying drawings, of which.

Figure 1:
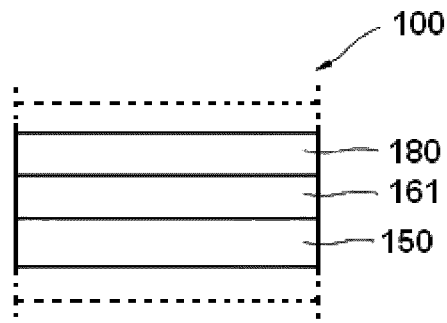
FIG. 1 is a schematic sectional view of an organic light-emitting diode (OLED), according to an exemplary embodiment of the present invention with an emission layer, one electron transport layer and an electron injection layer.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

The term "contacting sandwiched" refers to an arrangement of three layers whereby the layer in the middle is in direct contact with the two adjacent layers.

The organic light emitting diodes according to an embodiment of the present invention may include a hole transport region; an emission layer; and a first electron transport layer comprising a compound according to formula 1.

FIG. 1 is a schematic sectional view of an organic light-emitting diode 100, according to an exemplary embodiment of the present invention. The OLED 100 comprises an emission layer 150, an electron transport layer (ETL) 161 comprising triazine compound of formula 1 and an electron injection layer 180, whereby the first electron transport layer 161 is disposed directly on the emission layer 150 and the electron injection layer 180 is disposed directly on the first electron transport layer 161.

Figure 2:
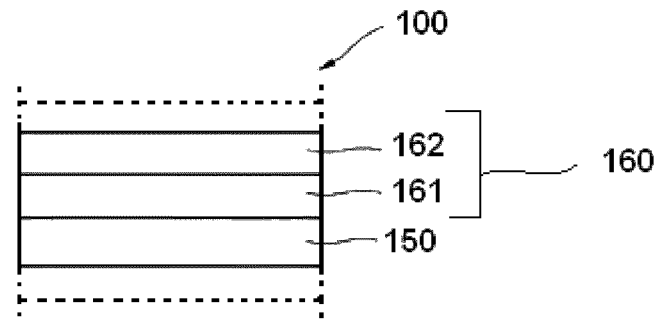
FIG. 2 is a schematic sectional view of an organic light-emitting diode (OLED), according to an exemplary embodiment of the present invention with an emission layer and two electron transport layers.

FIG. 2 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 comprising triazine compound of formula 1 and a second electron transport layer 162, whereby the second electron transport layer 162 is disposed directly on the first electron transport layer 161. Alternatively, the electron transport layer stack (ETL) 160 comprises a first electron transport layer 161 and a second electron transport layer 162 comprising a triazine compound of formula 1, whereby the second electron transport layer 162 is disposed directly on the first electron transport layer 161.

Figure 3:
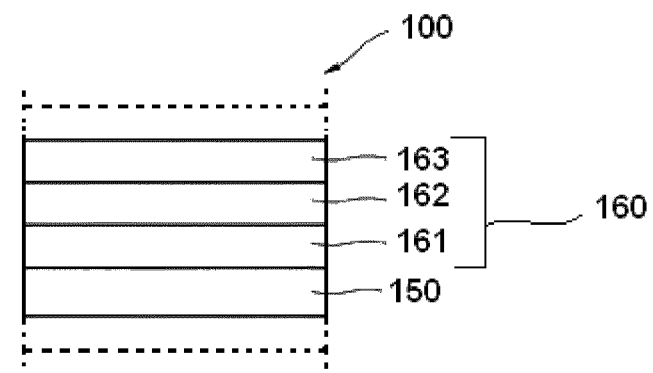
FIG. 3 is a schematic sectional view of an OLED, according to an exemplary embodiment of the present invention with an emission layer and three electron transport layers.

FIG. 3 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 that comprises triazine compound of formula 1, a second electron transport layer 162 that comprises triazine compound of formula 1 but different to the triazine compound of the first electron transport layer, and a third electron transport layer 163, whereby the second electron transport layer 162 is disposed directly on the first electron transport layer 161 and the third electron transport layer 163 is disposed directly on the first electron transport layer 162.

Figure 4:
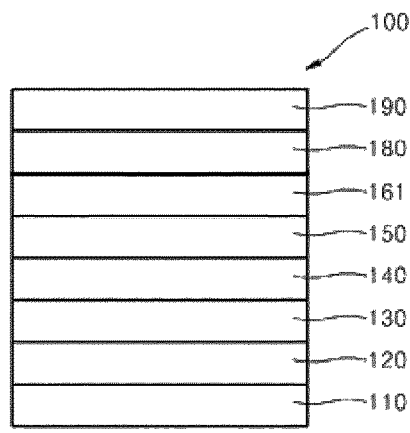
FIG. 4 is a schematic sectional view of an organic light-emitting diode (OLED), according to an exemplary embodiment of the present invention with an emission layer and one electron transport layer.

FIG. 4 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, one first electron transport layer (ETL) 161, an electron injection layer (EIL) 180, and a cathode electrode 190. The first electron transport layer (ETL) 161 comprises triazine compound of formula 1 and optionally an alkali halide or alkali organic complex. The electron transport layer (ETL) 161 is formed directly on the EML 150.

Figure 5:
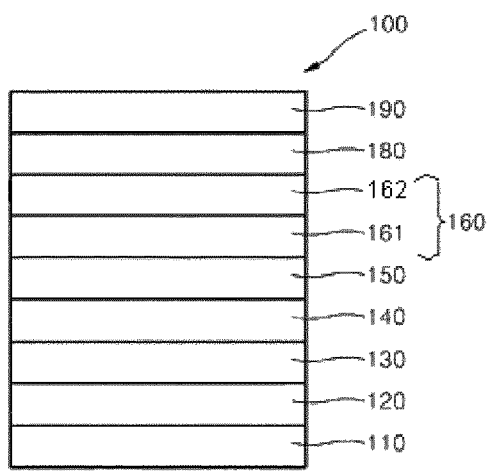
FIG. 5 is a schematic sectional view of an organic light-emitting diode (OLED), according to an exemplary embodiment of the present invention with an emission layer and two electron transport layers.

FIG. 5 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a cathode electrode 190. The electron transport layer (ETL) 160 comprises a first electron transport layer 161 and a second electron transport layer 162, wherein the first electron transport layer is arranged near to the anode (120) and the second electron transport layer is arranged near to the cathode (190). The first and/or the second electron transport layer comprise triazine compound of formula 1 and optionally an alkali halide or alkali organic complex.

Figure 6:
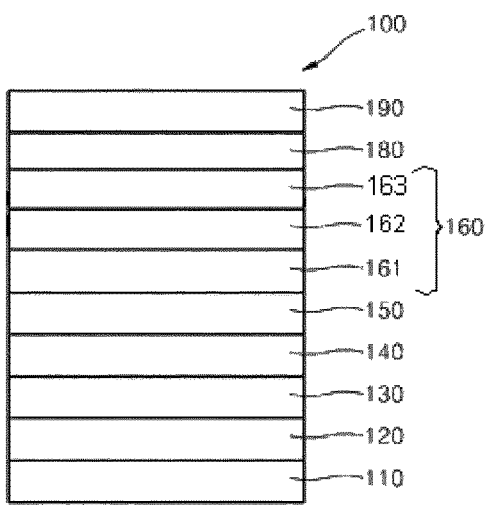
FIG. 6 is a schematic sectional view of an OLED, according to an exemplary embodiment of the present invention with an emission layer and three electron transport layers.

FIG. 6 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a second cathode electrode 190. The electron transport layer stack (ETL) 160 comprises a first electron transport layer 161, a second electron transport layer 162 and a third electron transport layer 163. The first electron transport layer 161 is formed directly on the emission layer (EML) 150. The first, second and/or third electron transport layer comprise triazine compound of formula 1 that is different for each layer, and optionally an alkali halide or alkali organic complex.

Organic Semiconductor Layer

According to another aspect an organic semiconductor layer may comprises at least one triazine compound of formula 1 and/or formula 1a.

According to one embodiment the organic semiconductor layer may comprises at least one triazine compound of formula 1 and further comprises a metal, metal salt or organic alkali metal complex, preferably alkali metal complex, more preferably LiQ or alkali borate.

According to one embodiment the organic semiconductor layer may comprises at least one triazine compound of formula 1 and further comprises a metal, metal salt or organic metal complex, preferably an organic monovalent or divalent metal complex, more preferably LiQ or alkali borate.

According to one embodiment the organic semiconductor layer may comprises at least one triazine compound of formula 1 and LiQ.

According to one embodiment the organic semiconductor layer may comprises at least one triazine compound of formula 1 and alkali borate.

According to one embodiment, wherein at least one organic semiconductor layer is arranged between the emission layer and the cathode, preferably between the auxiliary electron transport layer and the cathode.

In another embodiment, the organic semiconductor layer is arranged between the emission layer and the electron transport layer.

According to one embodiment, the organic semiconductor layer is arranged between the first and second emission layer. The organic semiconductor layer can be an electron transport layer, an emission layer, a hole blocking layer, a charge generation layer and/or an electron injection layer, preferably an electron transport layer or a charge generation layer, and more preferred an electron transport layer.

According to one embodiment, the organic semiconductor layer can be arranged between a photoactive layer and a cathode layer, preferably between an emission layer or light-absorbing layer and the cathode layer, preferably the organic semiconductor layer is an electron transport layer.

According to one embodiment, the organic semiconductor layer may comprise at least one alkali halide or alkali organic complex.

An organic semiconductor layer comprises a triazine compound according to formula 1 or 1a is essentially non-emissive or non-emitting.

Organic Electronic Device

An organic electronic device according to the invention comprises at least one organic semiconductor layer, wherein at least one organic semiconductor layer comprises a triazine compound according to formula 1.

An organic electronic device according to one embodiment, which comprises at least one organic semiconductor layer that comprises a triazine compound according to formula 1, wherein this layer is essentially non-emissive or non-emitting.

According to one embodiment, the organic electronic device may comprises at least one organic semiconductor layer comprising triazine compound of formula 1 that is an electron transport layer, an emission layer, a hole blocking layer, a charge generation layer and/or an electron injection layer, preferably an electron transport layer or a charge generation layer, more preferred an electron transport layer.

An organic electronic device according to one embodiment may include a substrate, an anode layer, an organic semiconductor layer comprising triazine compound of formula 1, and a cathode layer.

The organic electronic device according to according to one embodiment may comprises at least one organic semiconductor layer, wherein the organic semiconductor layer comprising triazine compound of formula 1 is arranged between a photoactive layer and a cathode layer, preferably between an emission layer or light-absorbing layer and the cathode layer, preferably the organic semiconductor layer is an electron transport layer The organic electronic device according to according to one embodiment may comprises at least one organic semiconductor layer comprising triazine compound of formula 1, wherein the at least one organic semiconductor layer further comprises at least one alkali halide or alkali organic complex.

An organic electronic device according to one embodiment comprises at least one organic semiconductor layer comprising at least one triazine compound of formula 1, at least one anode layer, at least one cathode layer and at least one emission layer, wherein the organic semiconductor layer comprising at least one triazine compound of formula 1 is preferably arranged between the emission layer and the cathode layer.

An organic electronic device according to one embodiment comprises at least one organic semiconductor layer comprising at least one triazine compound of formula 1 and further comprises at least one alkali halide or alkali organic complex.

An organic electronic device according to one embodiment comprises at least one organic semiconductor layer, at least one anode layer, at least one cathode layer and at least one emission layer, wherein the organic semiconductor layer comprising at least one triazine compound of formula 1 is preferably arranged between the emission layer and the cathode layer. Preferably the at least one organic semiconductor layer is an electron transport layer.

An organic light-emitting diode (OLED) according to the invention may include an anode, a hole transport layer (HTL), an emission layer (EML), an electron transport layer (ETL) comprising at least one triazine compound of formula 1, and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device. A light emitting device can be an OLED.

According to one embodiment the OLED may have the following layer structure, wherein the layers having the following order:

an anode layer, a hole injection layer, optional a first hole transport layer, optional a second hole transport layer, an emission layer, an electron transport layer comprising triazine compound of formula 1 according to the invention, an electron injection layer, and a cathode layer.

According to another aspect of the present invention, there is provided a method of manufacturing an organic electronic device, the method using:
  at least one deposition source, preferably two deposition sources and more preferred at least three deposition sources.
  The methods for deposition that can be suitable comprise:
  deposition via vacuum thermal evaporation;
  deposition via solution processing, preferably the processing is selected from spin-coating, printing, casting; and/or
  slot-die coating.

According to various embodiments of the present invention, there is provided a method using:
  a first deposition source to release the triazine compound of formula 1 according to the invention, and
  a second deposition source to release the alkali halide or alkali organic complex, preferably a lithium halide or lithium organic complex;
the method comprising the steps of forming the electron transport layer stack; whereby for an organic light-emitting diode (OLED):
  the first electron transport layer is formed by releasing the triazine compound of formula 1 according to the invention from the first deposition source and the alkali halide or alkali organic complex, preferably a lithium halide or lithium organic complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
  on a substrate a first anode electrode is formed,
  on the first anode electrode an emission layer is formed,
  on the emission layer an electron transport layer stack is formed, preferably a first electron transport layer is formed on the emission layer and a second electron transport layer is formed on the first electron transport layer and the second electron transport layer comprises a triazine compound of formula 1,
  and finally a cathode electrode is formed,
  optional a hole injection layer, a hole transport layer, and a hole blocking layer, formed in that order between the first anode electrode and the emission layer,
  optional an electron injection layer is formed between the electron transport layer stack and the cathode electrode.

According to various embodiments of the present invention, the method may further include forming an electron injection layer on a first electron transport layer. However, according to various embodiments of the OLED of the present invention, the OLED may not comprise an electron injection layer.

According to various embodiments, the OLED may have the following layer structure, wherein the layers having the following order:
an anode, first hole transport layer, second hole transport layer, emission layer, optional second electron transport layer, first electron transport layer comprising triazine compound of formula 1 according to the invention, optional a second electron transport layer, optional an electron injection layer, and a cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples. However, the present disclosure is not limited to the following examples. Reference will now be made in detail to the exemplary aspects.

Preparation of Triazine Compounds of Formula 1

Triazine compounds of formula 1 may be prepared as described below.

Preparation of 2-(dibenzo[b,d]furan-3-yl)-4-phenyl-6-(4'-phenyl-[1,1':2',1''-terphenyl]-4-yl)-1,3,5-triazine

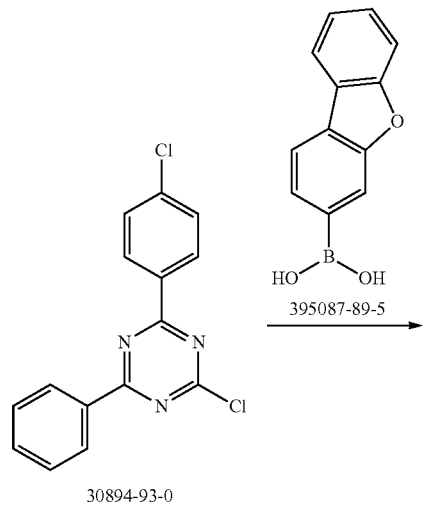

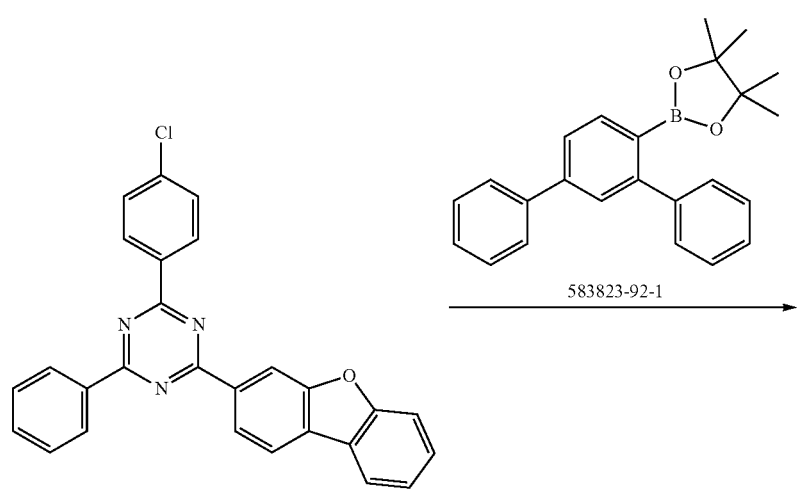

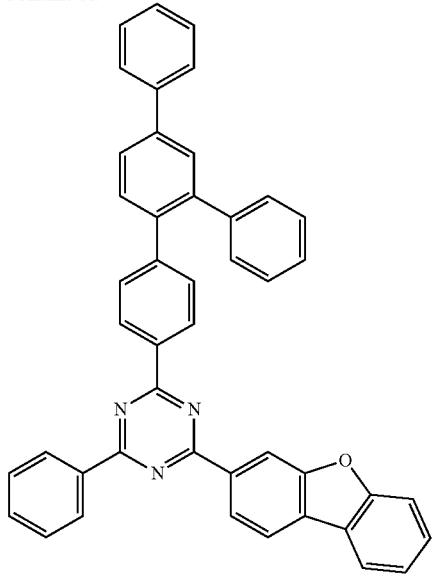

2-(4-chlorophenyl)-4-(dibenzo[b,d]furan-3-yl)-6-phenyl-1,3,5-triazine 2-(dibenzo[b,d]furan-3-yl)-4-phenyl-6-(4'-phenyl-[1,1':2',1''-terphenyl]-4-yl)-1,3,5-triazine

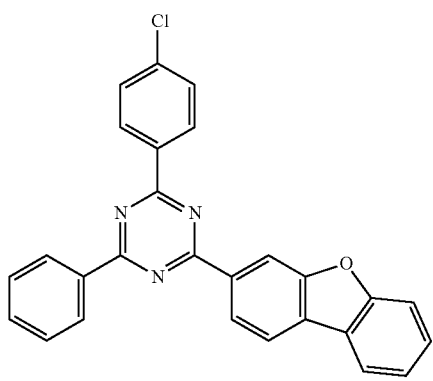 [SMILES: Clc1ccc(-c2nc(-c3ccccc3)nc(-c3ccc4c(c3)oc3ccccc34)n2)cc1]

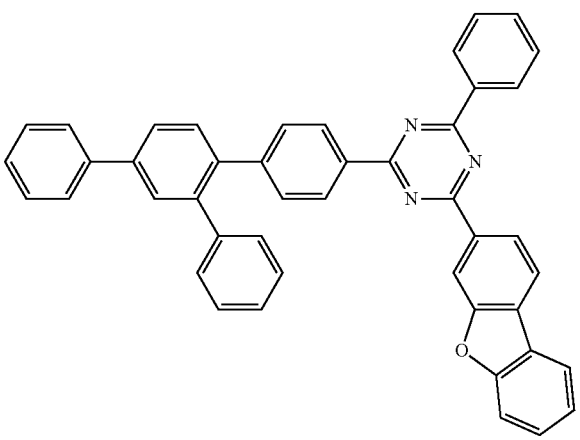 [SMILES: c1ccc(-c2ccc(-c3ccc(-c4nc(-c5ccccc5)nc(-c5ccc6c(c5)oc5ccccc56)n4)cc3)c(-c3ccccc3)c2)cc1]

A flask was flushed with nitrogen and charged with 2-chloro-4-(4-chlorophenyl)-6-phenyl-1,3,5-triazine (26.1 g, 86.3 mmol), dibenzo[b,d]furan-3-ylboronic acid (19.2 g, 90.7 mol), Pd(PPh$_3$)$_4$ (2.0 g, 1.73 mmol), and K$_2$CO$_3$ (23.8 g, 173.0 mmol). A mixture of deaerated THF/water (2:1, 405 mL) was added and the reaction mixture was heated to 75° C. under a nitrogen atmosphere for 5 h. After cooling down to 5° C., the resulting precipitate was isolated by suction filtration and washed with THF and n-hexane, followed by water and methanol. The crude product was dissolved in a mixture of hot chloroform and toluene (1:1), then n-hexane was added until precipitation begins. After stirring for 30 min at room temperature, the precipitate was collected by suction filtration and washed with n-hexane. After trituration with toluene and drying, 34.3 g (92%) of a pale yellow solid were obtained.

A flask was flushed with nitrogen and charged with 2-(4-chlorophenyl)-4-(dibenzo[b,d]furan-3-yl)-6-phenyl-1,3,5-triazine (11.2 g, 25.9 mmol), 2-([1,1':3',1''-terphenyl]-4'-yl)-4,4,5,5-tetramethyl-1,3,2-dioxaborolane (11.1 g, 31.1 mol), chloro(crotyl)(2-dicyclohexylphosphino-2',6'-dimethoxybiphenyl)palladium(II) (0.31 g, 0.51 mmol), and K$_3$PO$_4$ (11.0 g, 51.9 mmol). A mixture of deaerated THF/water (4:1, 250 mL) was added and the reaction mixture was heated to 50° C. under a nitrogen atmosphere for 17 h. After cooling down to room temperature, the resulting precipitate was isolated by suction filtration and washed with THF. The crude product was dissolved in chlorobenzene and filtered through a pad of Florisil. After rinsing with additional chlorobenzene, the filtrate was evaporated to dryness and the residue was triturated with methanol. Further purification was achieved by recrystallization from chlorobenzene and o-xylene to yield 7.5 g (46%) of a white solid after drying. Final purification was achieved by sublimation. m/z=628 ([M+H]$^+$).

Preparation of 2-(dibenzo[b,d]furan-3-yl)-4-(2',6'-diphenyl-[1,1':4',1''-terphenyl]-4-yl)-6-phenyl-1,3,5-triazine

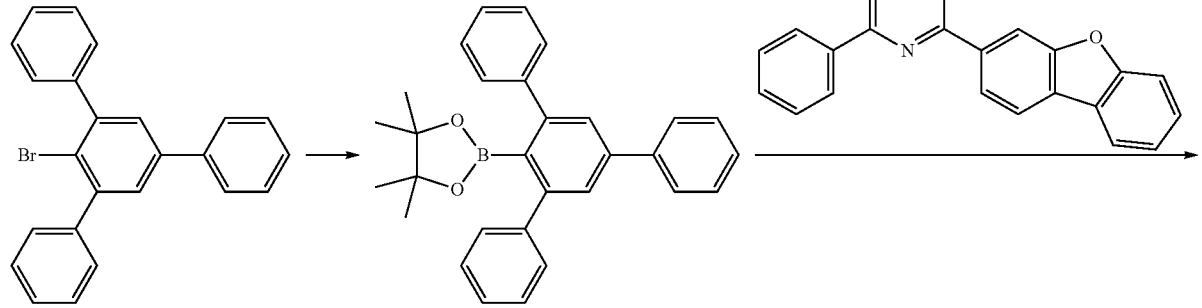

10368-73-7

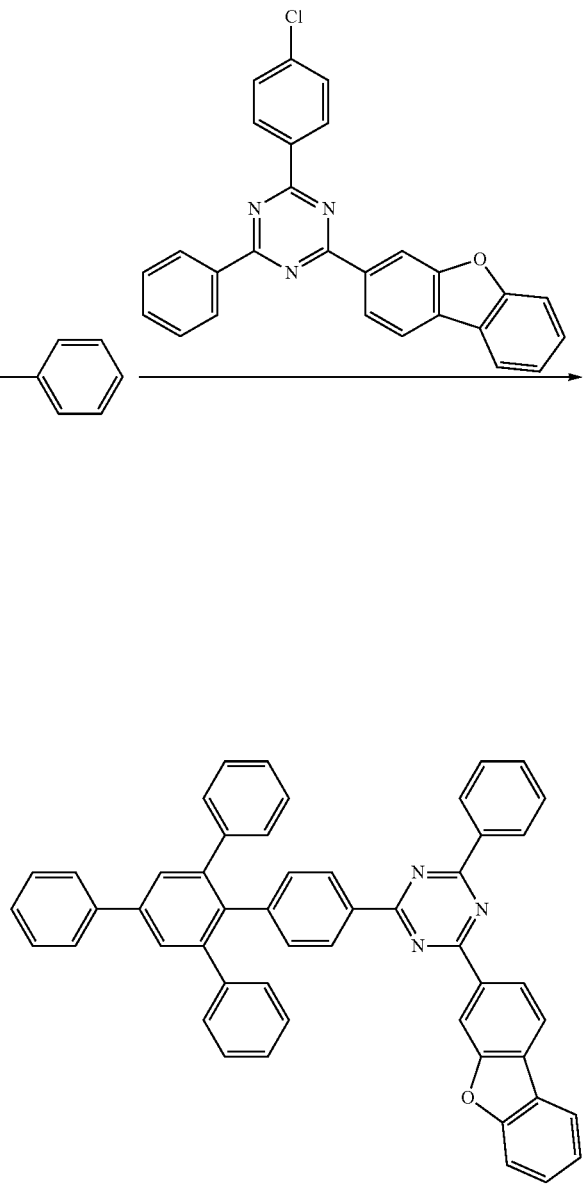

4,4,5,5-tetramethyl-2-(5'-phenyl-[1,1':3',1''-terphenyl]-2'-yl)-1,3,2-dioxaborolane

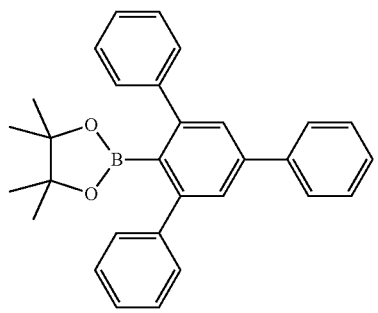 [SMILES: CC1(C)OB(c2c(-c3ccccc3)cc(-c3ccccc3)cc2-c2ccccc2)OC1(C)C]

To a stirred solution of 2'-bromo-5'-phenyl-1,1':3',1''-terphenyl (60.0 g, 155.7 mmol) in THF (950 mL) at −80° C. was added n-butyllithium in n-hexane (129.6 mL, 33 wt %, 323.9 mmol) and the mixture was slowly warmed up to −60° C. during 4 hours. The green solution was then cooled down to −80° C. and 2-isopropoxy-4,4,5,5-tetramethyl-1,3,2-dioxaborolane (86.9 g, 467.2 mmol) was added slowly. The mixture was stirred overnight while the temperature gradually increased to room temperature. Methanol was added and the crude reaction mixture was evaporated to dryness. The residue was dissolved in chloroform and extracted with water three times. The organic phase was dried over MgSO$_4$, filtered and evaporated to dryness. After trituration with n-hexane and drying, 42.2 g (62%) of a white solid were obtained.

2-(dibenzo[b,d]furan-3-yl)-4-(2',6'-diphenyl-[1,1':4',1''-terphenyl]-4-yl)-6-phenyl-1,3,5-triazine

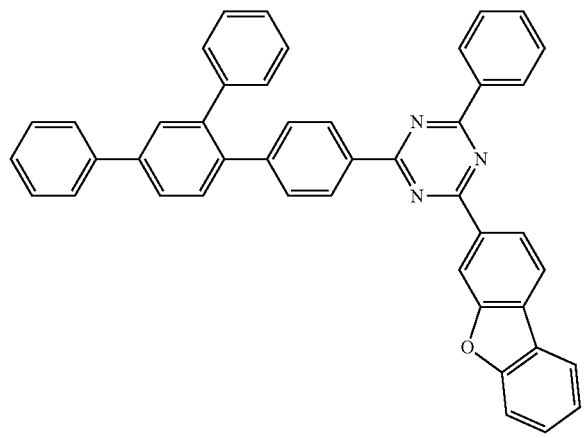 [SMILES: c1ccc(-c2ccc(-c3ccc(-c4nc(-c5ccccc5)nc(-c5ccc6c(c5)oc5ccccc56)n4)cc3)c(-c3ccccc3)c2)cc1]

A flask was flushed with nitrogen and charged with 2-(4-chlorophenyl)-4-(dibenzo[b,d]furan-3-yl)-6-phenyl-1,3,5-triazine (10.0 g, 23 mmol), 4,4,5,5-tetramethyl-2-(5'-phenyl-[1,1':3',1''-terphenyl]-2'-yl)-1,3,2-dioxaborolane (12.0 g, 27.7 mol), chloro(crotyl)(2-dicyclohexylphosphino-2',6'-dimethoxybiphenyl)palladium(II) (0.28 g, 0.46 mmol), and K$_3$PO$_4$ (9.8 g, 46.1 mmol). A mixture of deaerated THF/water (4:1, 290 mL) was added and the reaction mixture was heated to 50° C. under a nitrogen atmosphere for two days. Additional chloro(crotyl)(2-dicyclohexylphosphino-2',6'-dimethoxybiphenyl)-palladium(II) (0.28 g, 0.46 mmol) was added and the reaction mixture was heated to 70° C. under a nitrogen atmosphere for five days. After cooling down to room temperature, the formed precipitate was collected by suction filtration and washed with water and methanol. The crude product was dissolved in hot chlorobenzene and filtered through a pad of silica gel. After rinsing with additional hot chlorobenzene, the combined filtrates were concentrated in vacuo and the obtained precipitate was isolated by suction filtration and washed with n-hexane. After recrystallization from THF and drying, 4.1 g (27%) of a pale yellow solid were obtained. Final purification was achieved by sublimation. m/z=704 ([M+H]$^+$).

Preparation of 2-(dibenzo[b,d]furan-3-yl)-4-(3',5'-diphenyl-[1,1':4',1''-terphenyl]-4-yl)-6-phenyl-1,3,5-triazine

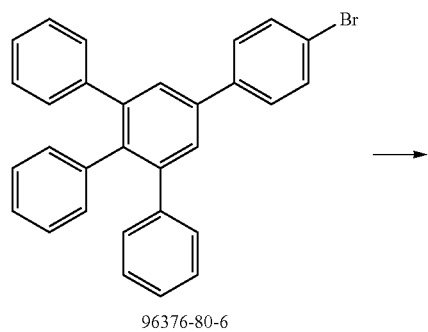

96376-80-6

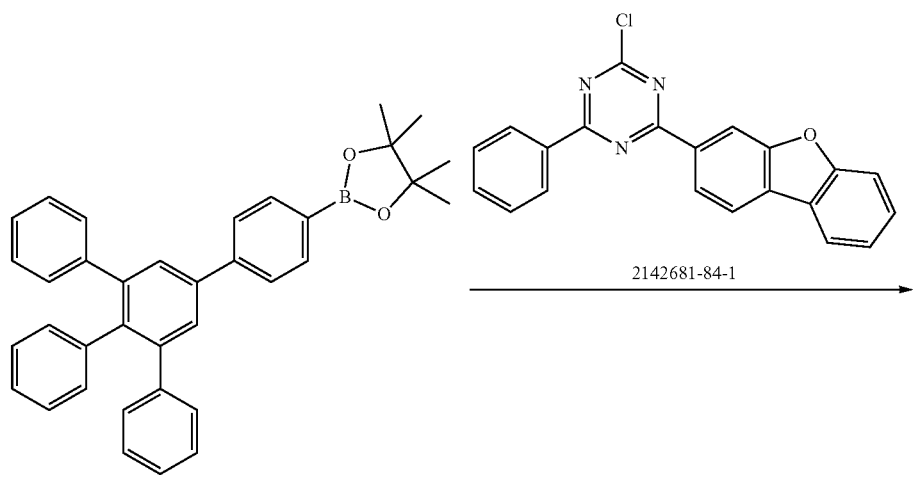

2142681-84-1

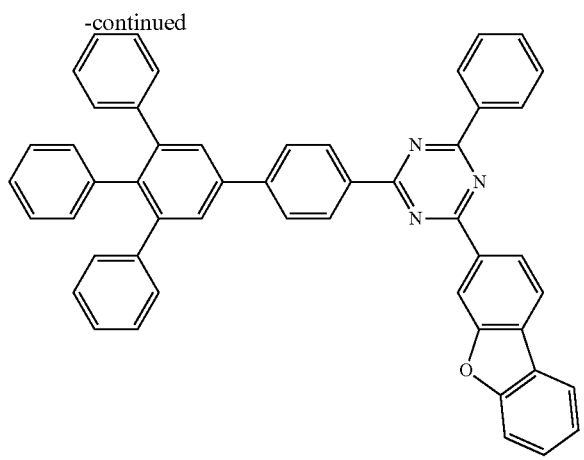

2-(3',5'-diphenyl-[1,1':4',1''-terphenyl]-4-yl)-4,4,5,5-tetramethyl-1,3,2-dioxaborolane

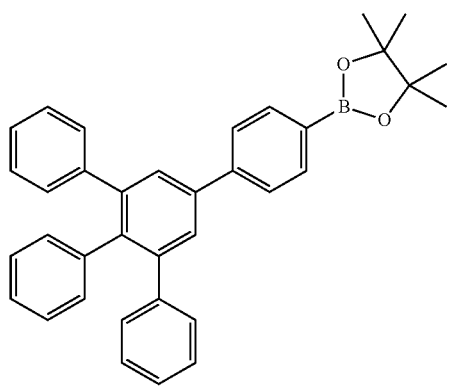 [SMILES: CC1(C)OB(c2ccc(-c3cc(-c4ccccc4)c(-c4ccccc4)c(-c4ccccc4)c3)cc2)OC1(C)C]

A flask was flushed with nitrogen and charged with 5'-(4-bromophenyl)-3'-phenyl-1,1':2',1''-terphenyl (11.0 g, 23.8 mmol), bis(pinacolato)diboron (6.7 g, 26.2 mmol), Pd(dppf)Cl$_2$ (1.0 g, 1.4 mmol), and potassium acetate (5.8 g, 59.6 mmol). Dry and deaerated DMF (110 mL) was added and the reaction mixture was heated to 80° C. under a nitrogen atmosphere for 22 hours. Subsequently, all volatiles were removed in vacuo, water and dichloromethane were added and the organic phase was washed with water four times. After drying over MgSO$_4$, the organic phase was filtered through a pad of Florisil. After rinsing with additional dichloromethane, the filtrate was concentrated to a minimal amount and precipitation was induced by addition of n-hexane. The precipitate was collected by suction filtration, washed with n-hexane and dried to yield 10.4 g (86%) of an off-white solid.

2-(dibenzo[b,d]furan-3-yl)-4-(3',5'-diphenyl-[1,1':4',1''-terphenyl]-4-yl)-6-phenyl-1,3,5-triazine

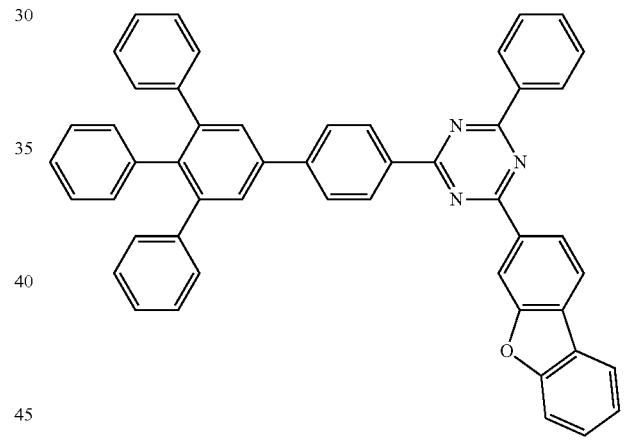

A flask was flushed with nitrogen and charged with 2-(3',5'-diphenyl-[1,1':4',1''-terphenyl]-4-yl)-4,4,5,5-tetramethyl-1,3,2-dioxaborolane (5.0 g, 9.8 mmol), 2-chloro-4-(dibenzo[b,d]furan-3-yl)-6-phenyl-1,3,5-triazine (7.1 g, 20.0 mol), Pd(PPh$_3$)$_4$ (0.48 g, 0.42 mmol), and K$_2$CO$_3$ (5.8 g, 41.9 mmol). A mixture of deaerated 1,4-dioxane/water (5:1, 120 mL) was added and the reaction mixture was heated to reflux under a nitrogen atmosphere overnight. After cooling down to room temperature, the formed precipitate was collected by suction filtration and washed with water, methanol and n-hexane. The crude product was dissolved in hot toluene and filtered through a pad of silica gel. After rinsing with additional hot toluene, the combined filtrates were concentrated in vacuo and, after the addition of n-hexane, the obtained precipitate was isolated by suction filtration and washed with n-hexane. After trituration with toluene and drying, 4.0 g (29%) of a white solid were obtained. Final purification was achieved by sublimation. m/z=704 ([M+H]$^+$).

Preparation of 2-(dibenzo[b,d]furan-3-yl)-4-phenyl-6-(4',5',6'-triphenyl-[1,1':2',1":4",1'''-quaterphenyl]-4'''-yl)-1,3,5-triazine
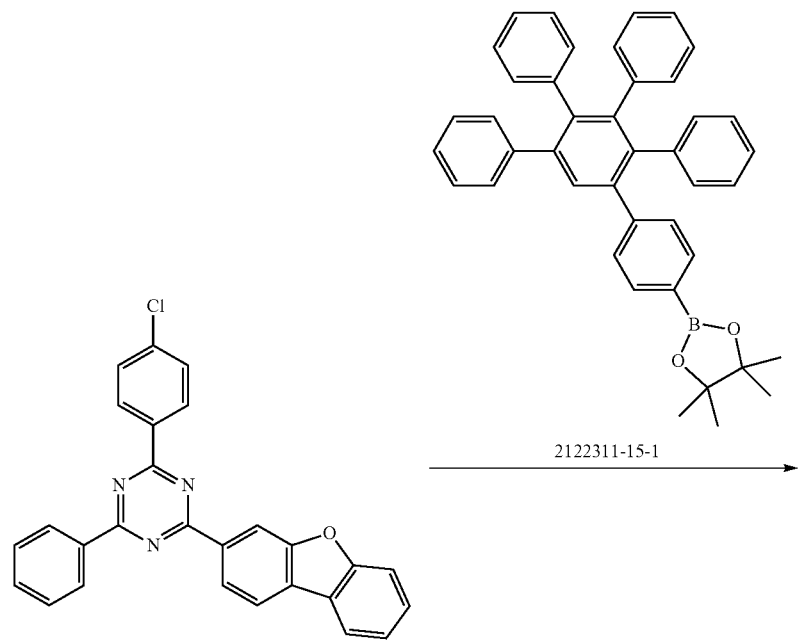
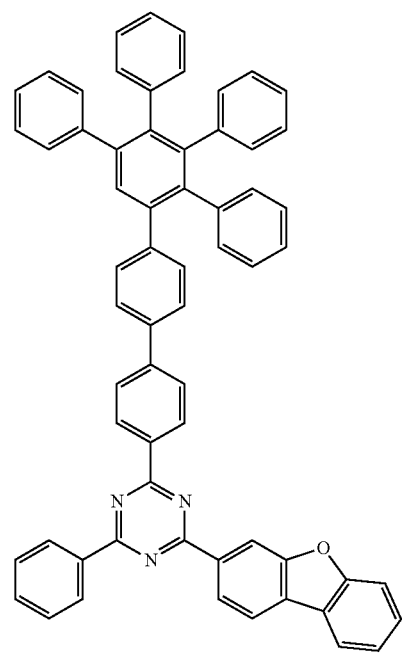 [SMILES: c1ccc(-c2nc(-c3ccc(-c4ccc(-c5cc(-c6ccccc6)c(-c6ccccc6)c(-c6ccccc6)c5-c5ccccc5)cc4)cc3)nc(-c3ccc4c(c3)oc3ccccc34)n2)cc1]

2-(dibenzo[b,d]furan-3-yl)-4-phenyl-6-(4',5',6'-triphenyl-[1,1':2',1":4",1"'-quaterphenyl]-4"'-yl)-1,3,5-triazine

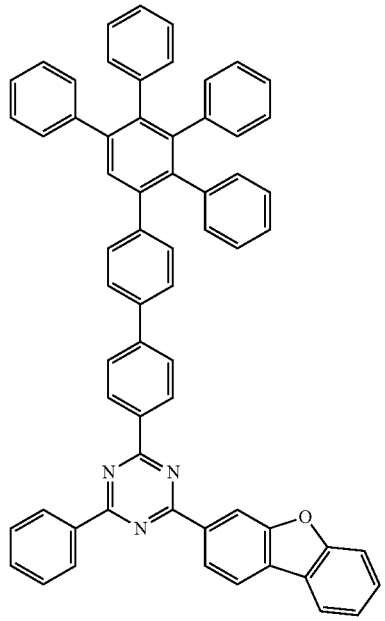

A flask was flushed with nitrogen and charged with 2-(4-chlorophenyl)-4-(dibenzo[b,d]furan-3-yl)-6-phenyl-1,3,5-triazine (15 g, 34.6 mmol), 4,4,5,5-tetramethyl-2-(3',4',5'-triphenyl-[1,1':2',1"-terphenyl]-4-yl)-1,3,2-dioxaborolane (30.4 g, 52 mmol), chloro(crotyl)(2-dicyclohexylphosphino-2',6'-dimethoxybiphenyl)-palladium(II) (0.63 g, 1.04 mmol), and $K_3PO_4$ (14.7 g, 69 mmol). A mixture of deaerated THF/water (4:1, 375 mL) was added and the reaction mixture was heated to 45° C. under a nitrogen atmosphere for 46 h. Subsequently, all volatiles were removed in vacuo and the residue was dissolved in dichloromethane/water. The aqueous phase was removed and the organic phase was washed with water four times, dried over $MgSO_4$ and filtered over a pad of florisil. The filtrate was concentrated in vacuo and acetonitrile was added. The formed precipitate was collected by suction filtration and washed with acetonitrile. After trituration with ethyl acetate and drying in vacuo, 25.7 g (87%) of a white solid were obtained. Final purification was achieved by sublimation. m/z=856 ([M+H]$^+$).

Scheme for the Preparation of Triazine Compound of Formula 1 with a, b and c=1:

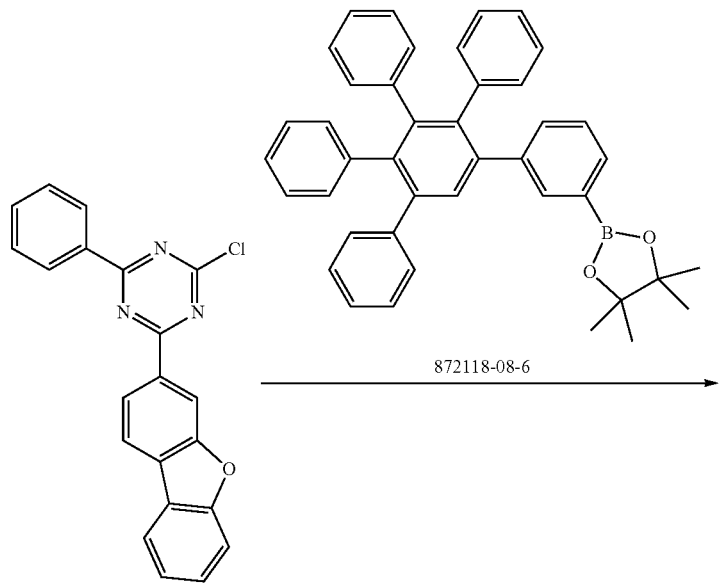

-continued
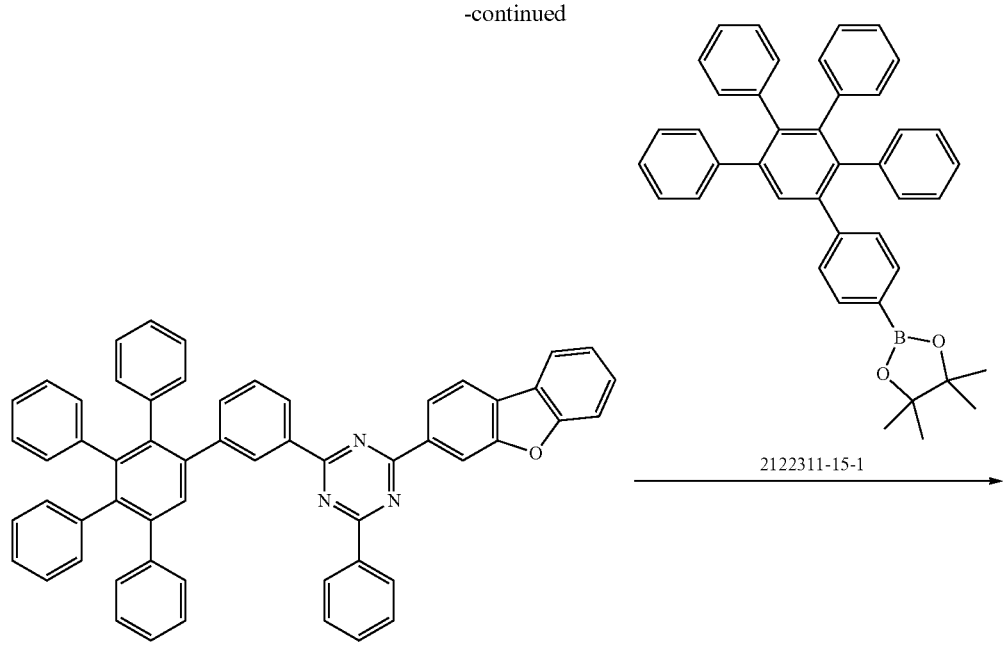
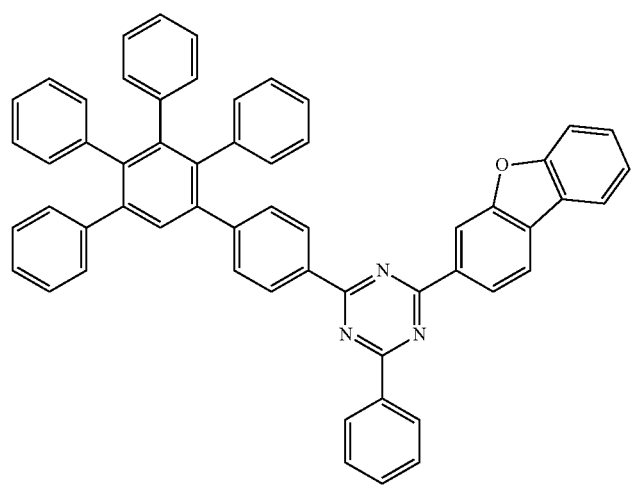

57

2-(dibenzo[b,d]furan-3-yl)-4-phenyl-6-(3',4',5'-triphenyl-[1,1':2',1''-terphenyl]-3-yl)-1,3,5-triazine

58

2-(dibenzo[b,d]furan-3-yl)-4-phenyl-6-(3',4',5'-triphenyl-[1,1':2',1''-terphenyl]-4-yl)-1,3,5-triazine

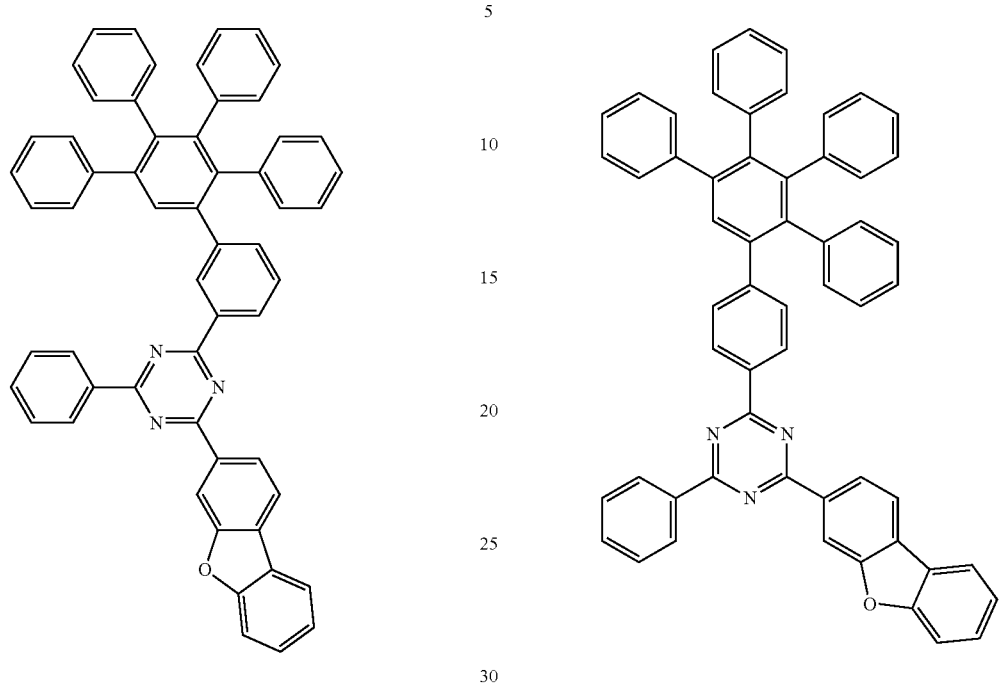

A flask was flushed with nitrogen and charged with 2-chloro-4-(dibenzo[b,d]furan-3-yl)-6-phenyl-1,3,5-triazine (10 g, 27.9 mmol), 4,4,5,5-tetramethyl-2-(3',4',5'-triphenyl-[1,1':2',1''-terphenyl]-3-yl)-1,3,2-dioxaborolane (17.2 g, 29.4 mmol), Pd(PPh$_3$)$_4$ (0.65 g, 0.56 mmol), and K$_2$CO$_3$ (7.7 g, 55.8 mmol). A mixture of deaerated THF/water (2:1, 200 mL) was added and the reaction mixture was heated to reflux under a nitrogen atmosphere for 26 h. After cooling down to 10° C., the formed precipitate was collected by suction filtration and washed with THF and n-hexane. The solid was dissolved in chloroform and the organic phase was extracted with water three times, dried over MgSO$_4$ and filtered through a pad of silica gel and florisil. The filtrate was concentrated in vacuo and n-hexane was added. The formed precipitate was collected by suction filtration and washed with n-hexane. After trituration with toluene and drying in vacuo, 15.8 g (72%) of a white solid were obtained. Final purification was achieved by sublimation. m/z=780 ([M+H]$^+$).

Following the procedure described above using 2-chloro-4-(dibenzo[b,d]furan-3-yl)-6-phenyl-1,3,5-triazine (10 g, 27.9 mmol), 4,4,5,5-tetramethyl-2-(3',4',5'-triphenyl-[1,1':2', 1''-terphenyl]-4-yl)-1,3,2-dioxaborolane (18 g, 30.7 mmol), Pd(PPh$_3$)$_4$ (0.65 g, 0.56 mmol), K$_2$CO$_3$ (7.7 g, 55.8 mmol), THF/water (2:1, 200 mL), and 20 h reaction time, 14.3 g (65%) of a white solid were obtained. Final purification was achieved by sublimation. m/z=780 ([M+H]$^+$).

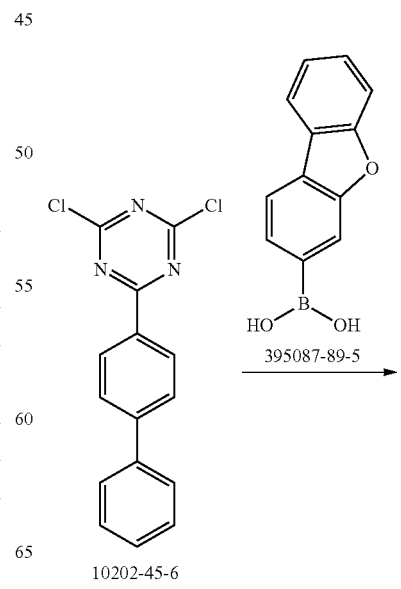

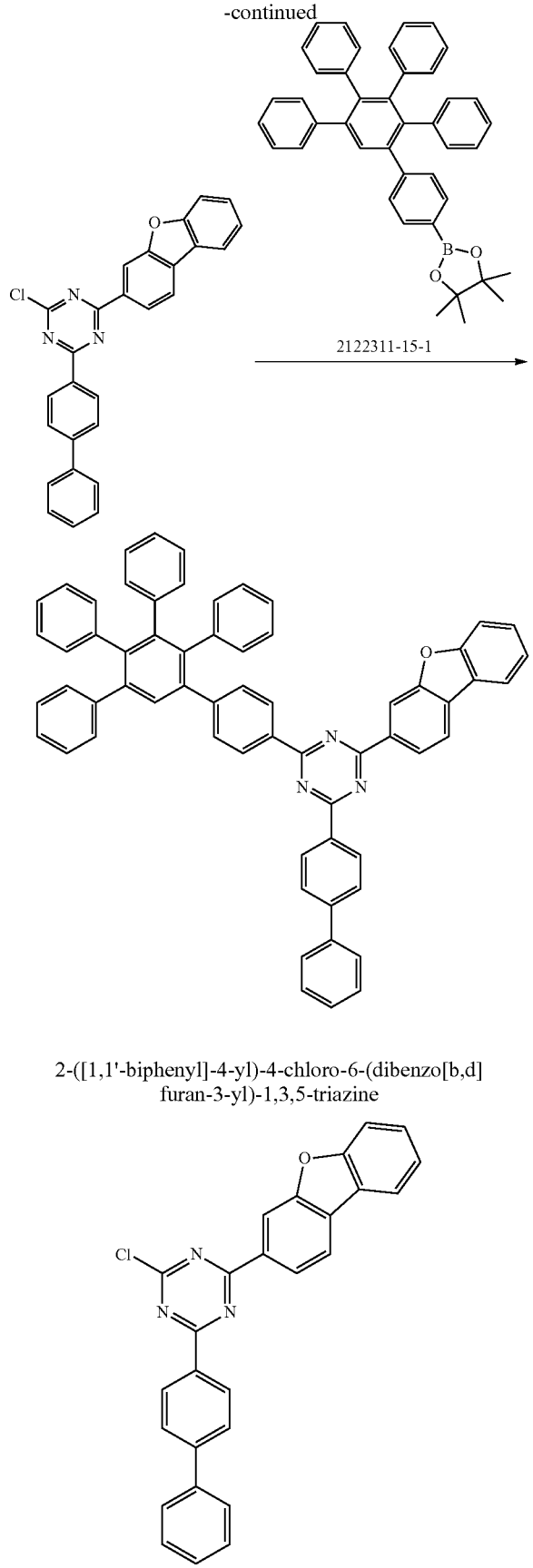

2-([1,1'-biphenyl]-4-yl)-4-chloro-6-(dibenzo[b,d]furan-3-yl)-1,3,5-triazine

A flask was flushed with nitrogen and charged with 2-([1,1'-biphenyl]-4-yl)-4,6-dichloro-1,3,5-triazine (80 g, 264.8 mmol), dibenzo[b,d]furan-3-ylboronic acid (44.9 g, 211.8 mmol), Pd(PPh$_3$)$_4$ (15.3 g, 13.2 mmol), and K$_2$CO$_3$ (91.5 g, 662 mmol). A mixture of deaerated toluene/THF/water (1:1:1, 1200 mL) was added and the reaction mixture was heated to 65° C. under a nitrogen atmosphere for 6 h. After cooling down to room temperature, the precipitate was collected by suction filtration and washed with water and toluene. The solid was dissolved in hot toluene and filtered through a pad of silica gel. The filtrate was allowed to cool down to room temperature and the resulting precipitate was collected by suction filtration and washed toluene. After drying in vacuo, 32.7 g (28%) of a white solid were obtained. Final purification was achieved by sublimation.

2-([1,1'-biphenyl]-4-yl)-4-(dibenzo[b,d]furan-3-yl)-6-(3',4',5'-triphenyl-[1,1':2',1''-terphenyl]-4-yl)-1,3,5-triazine

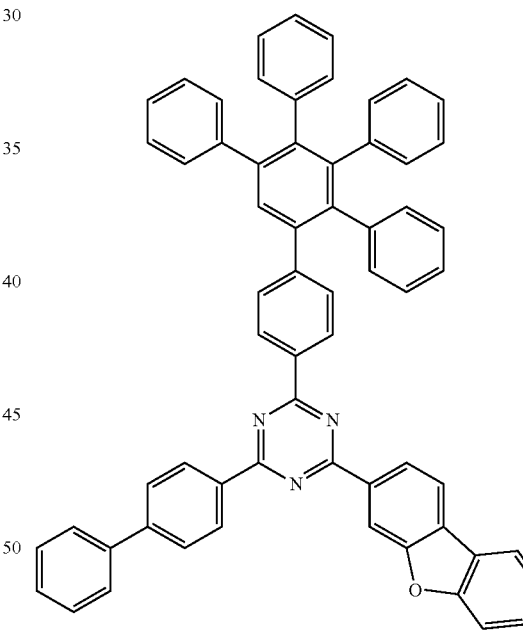

Following the procedure described above using 2-([1,1'-biphenyl]-4-yl)-4-chloro-6-(dibenzo[b,d]furan-3-yl)-1,3,5-triazine (18 g, 41.5 mmol), 4,4,5,5-tetramethyl-2-(3',4',5'-triphenyl-[1,1':2',1''-terphenyl]-4-yl)-1,3,2-dioxaborolane (26.7 g, 45.6 mmol), Pd(PPh$_3$)$_4$ (0.96 g, 0.83 mmol), K$_2$CO$_3$ (11.5 g, 83 mmol), THF/water (4:1, 500 mL), and 21 h reaction time, 25.9 g (73%) of a white solid were obtained. Final purification was achieved by sublimation. m/z=856 ([M+H]$^+$).

61

Preparation of 2-(Dibenzo[b,d]furan-3-yl)-4-(naphthalen-2-yl)-6-(3',4',5'-triphenyl-[1,1':2',1''-terphenyl]-4-yl)-1,3,5-triazine

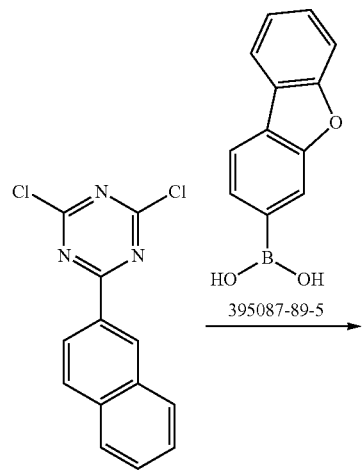

112719-97-8    395087-89-5

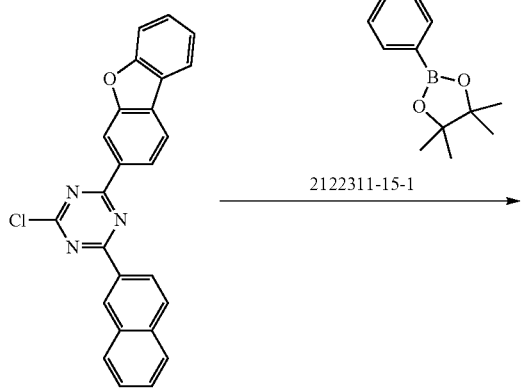

2122311-15-1

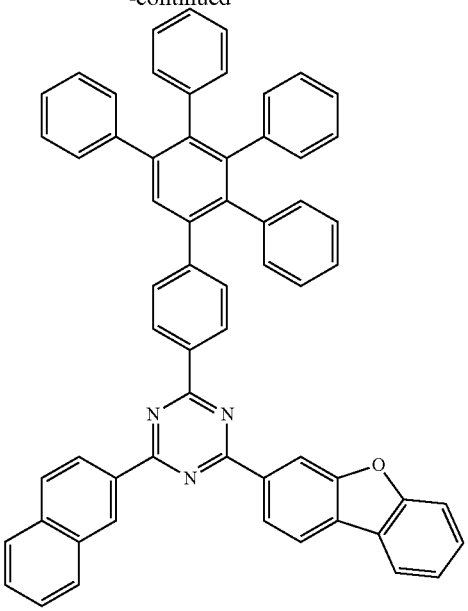

2-Chloro-4-(dibenzo[b,d]furan-3-yl)-6-(naphthalen-2-yl)-1,3,5-triazine

A flask was flushed with nitrogen and charged with 2,4-dichloro-6-(naphthalen-2-yl)-1,3,5-triazine (32.9 g, 119.1 mmol), dibenzo[b,d]furan-3-ylboronic acid (25.3 g, 119.1 mol) and $K_2CO_3$ (41.2 g, 297.8 mmol). A mixture of deaerated toluene/ethanol/water (1:1:1, 495 mL) was added followed by Pd(PPh$_3$)$_4$ (6.88 g, 5.9 mmol). The reaction mixture was heated to 45° C. under nitrogen atmosphere for 7 h. The reaction mixture was cooled with an ice bath, the precipitate collected by suction filtration and washed with toluene, water and methanol. Drying under vacuum yielded 26.1 g (54%) of an off-white solid.

2-(Dibenzo[b,d]furan-3-yl)-4-(naphthalen-2-yl)-6-(3',4',5'-triphenyl-[1,1':2',1''-terphenyl]-4-yl)-1,3,5-triazine

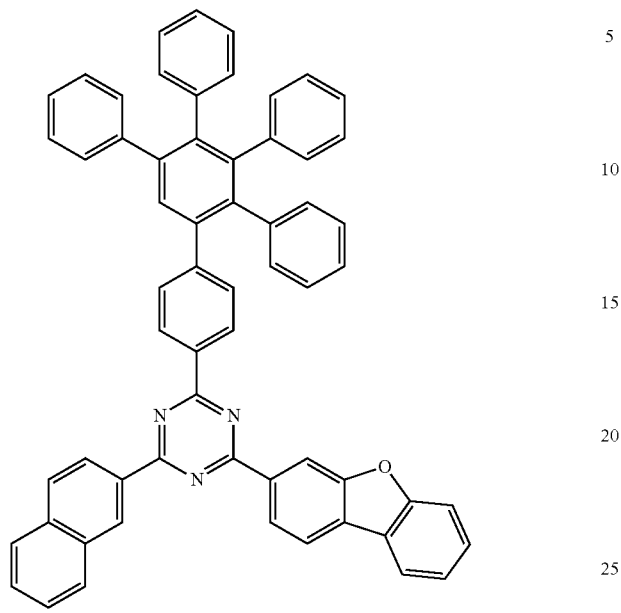

Following the general procedure described above using 2-Chloro-4-(dibenzo[b,d]furan-3-yl)-6-(naphthalen-2-yl)-1,3,5-triazine (20 g, 49 mmol), 4,4,5,5-tetramethyl-2-(3',4',5'-triphenyl-[1,1':2',1''-terphenyl]-4-yl)-1,3,2-dioxaborolane (31.5 g, 53.9 mol), $K_2CO_3$ (13.5 g, 98.1 mmol), $Pd(PPh_3)_4$ (1.13 g, 0.98 mmol), THF/water (4:1, 500 mL), and 3 d reaction time, 38 g (93%) of a pale yellow solid were obtained. Final purification was achieved by sublimation. m/z=830 ([M+H]$^+$).

Preparation of 2,4-di([1,1'-biphenyl]-4-yl)-6-(3',4',5'-triphenyl-[1,1':2',1''-terphenyl]-4-yl)-1,3,5-triazine

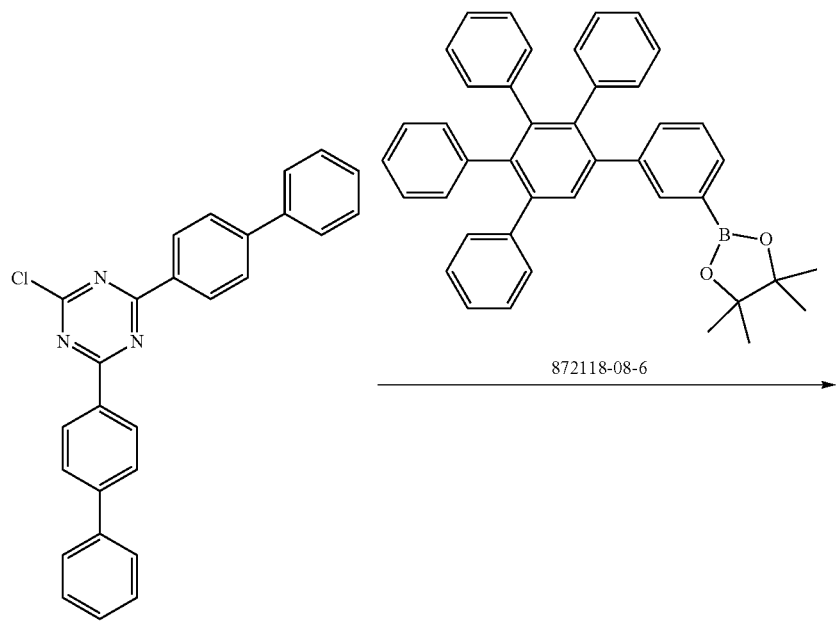

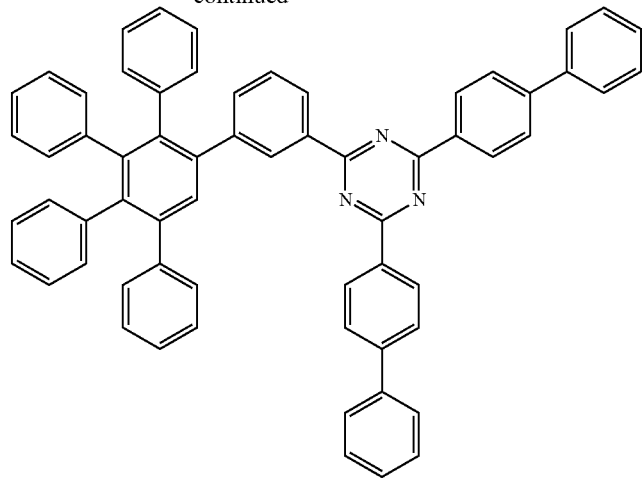

2,4-di([1,1'-biphenyl]-4-yl)-6-(3',4',5'-triphenyl-[1,1':2',1''-terphenyl]-4-yl)-1,3,5-triazine

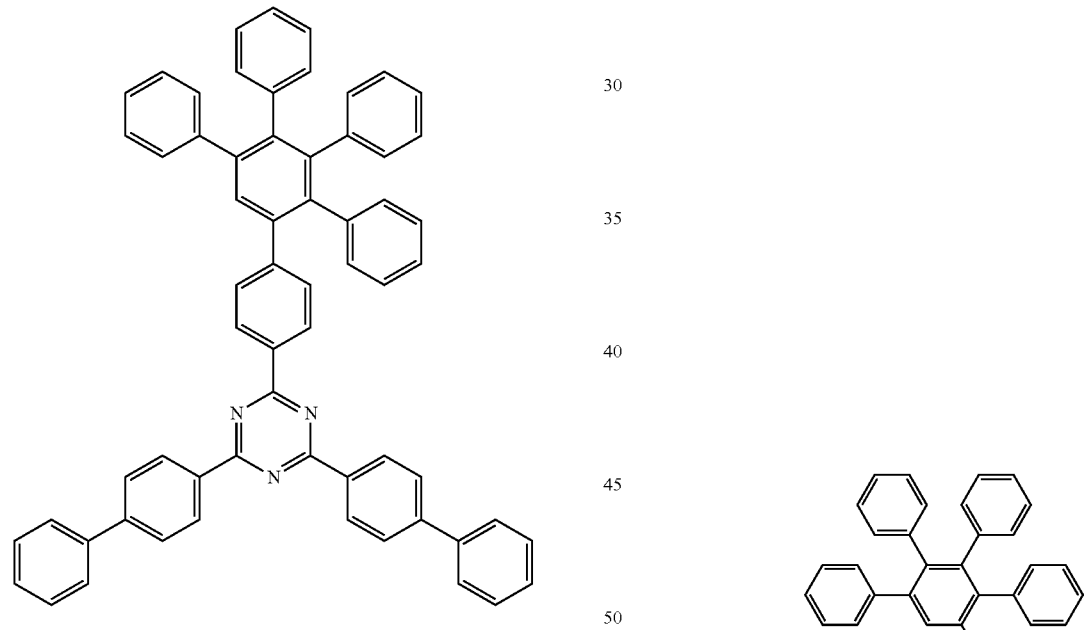

Following the general procedure described above using 2,4-di([1,1'-biphenyl]-4-yl)-6-chloro-1,3,5-triazine (10 g, 23.8 mmol), 4,4,5,5-tetramethyl-2-(3',4',5'-triphenyl-[1,1':2',1''-terphenyl]-3-yl)-1,3,2-dioxaborolane (14.6 g, 25 mmol), Pd(dppf)Cl$_2$ (0.87 g, 1.2 mmol), K$_2$CO$_3$ (6.57 g, 47.6 mmol), toluene/ethanol/water (9:3:2, 160 mL), and 2.5 h reaction time, 16.0 g (80%) of a white solid were obtained after repeated precipitation from dichloromethane with tert.-butyl methyl ether. Final purification was achieved by sublimation. m/z=842 ([M+H]$^+$).

Preparation of 2,4-Bis(dibenzo[b,d]furan-3-yl)-6-(3',4',5'-triphenyl-[1,1':2',1''-terphenyl]-4-yl)-1,3,5-triazine

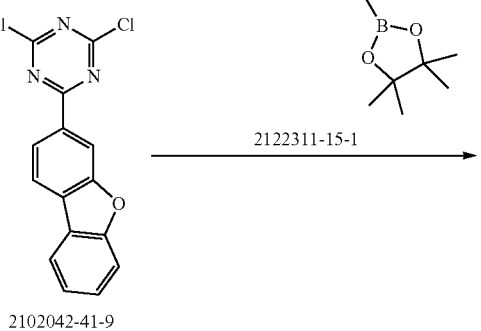

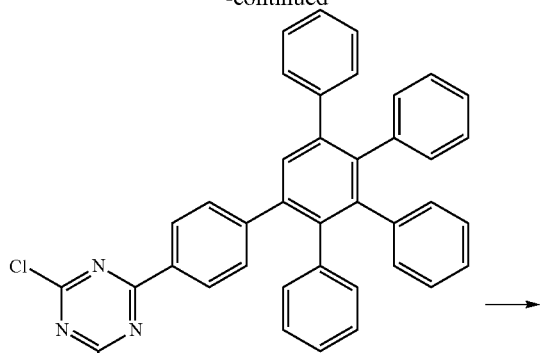

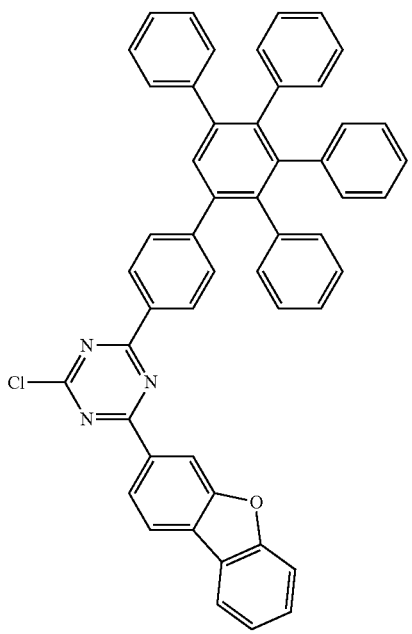 [SMILES: Clc1nc(-c2ccc(-c3cc(-c4ccccc4)c(-c4ccccc4)c(-c4ccccc4)c3-c3ccccc3)cc2)nc(-c2ccc3c(c2)oc2ccccc23)n1]

2-Chloro-4-(dibenzo[b,d]furan-3-yl)-6-(3',4',5'-triphenyl-[1,1':2',1''-terphenyl]-4-yl)-1,3,5-triazine A flask was flushed with nitrogen and charged with 2,4-dichloro-6-(dibenzo[b,d]furan-3-yl)-1,3,5-triazine (40.5 g, 128.3 mmol), 4,4,5,5-tetra-methyl-2-(3',4',5'-triphenyl-[1,1':2',1''-terphenyl]-4-yl)-1,3,2-dioxaborolane (60 g, 102.6 mol), Pd(dppf)Cl$_2$ (4.69 g, 6.41 mmol), and K$_2$CO$_3$ (44.2 g, 320 mmol). A mixture of deaerated toluene/THF/water (1:1:1, 1050 mL) was added and the reaction mixture was heated to 65° C. under a nitrogen atmosphere for 21 h. Then the mixture was allowed to cool to room temperature and the precipitate was collected by suction filtration. The solid was washed with water and n-hexane and dried in vacuo. Then the solid was suspended in dichloromethane and stirred overnight. After filtration, the solid was dried again in vacuo to yield 29.3 g (39%) of beige solid.

2,4-Bis(dibenzo[b,d]furan-3-yl)-6-(3',4',5'-triphenyl-[1,1':2',1''-terphenyl]-4-yl)-1,3,5-triazine

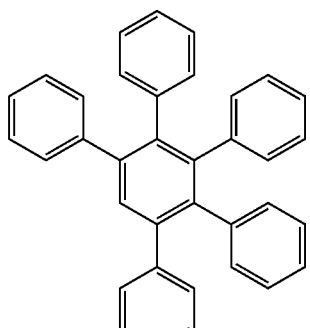

A flask was flushed with nitrogen and charged with 2-chloro-4-(dibenzo[b,d]furan-3-yl)-6-(3',4',5'-triphenyl-[1,1':2',1-terphenyl]-4-yl)-1,3,5-triazine (15 g, 20.3 mmol), dibenzo[b,d]furan-3-ylboronic acid (5.17 g, 24.3 mol), Pd(dppf)Cl$_2$ (0.29 g, 0.4 mmol), and K$_2$CO$_3$ (5.61 g, 40.6 mmol). A mixture of deaerated THF/water (4.3:1, 185 mL) was added and the reaction mixture was heated to 75° C. under a nitrogen atmosphere for 2 h. Additional 200 mL deaerated THF were added to the suspension and heating and stirring continued for 18 h. After cooling to room temperature, the precipitate was collected by suction filtration and washed with THF and water. The solid was triturated with hot chloroform. Subsequently, the solid was dissolved in hot chlorobenzene and filtered through a pad of silica gel. The filtrate was concentrated under reduced pressure and the obtained precipitate isolated by suction filtration. After drying in vacuo, 8.7 g (50° C.) of a white solid were obtained. Final purification was achieved by sublimation. m/z=870 ([M+H]$^+$).

The chemical structure, calculated HOMO, LUMO and dipole moment of compounds of formula 1 and comparative example ETM-1 are shown in Table 1.

TABLE 1
| Referred to as: | Structure | Calculated HOMO (eV) | Calculated LUMO (eV) | Dipole moment (Debye) |
|---|---|---|---|---|
| ETM-1 | 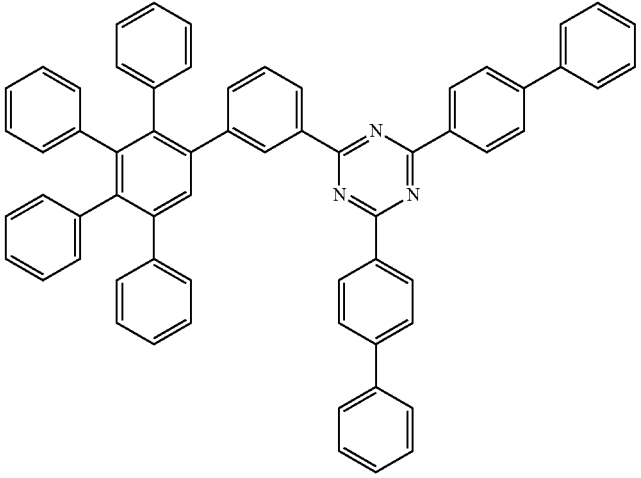 [SMILES: c1ccc(-c2ccc(-c3nc(-c4ccc(-c5ccccc5)cc4)nc(-c4cccc(-c5cc(-c6ccccc6)c(-c6ccccc6)c(-c6ccccc6)c5-c5ccccc5)c4)n3)cc2)cc1] | −5.81 | −1.86 | 0.60 |
| MX1 | 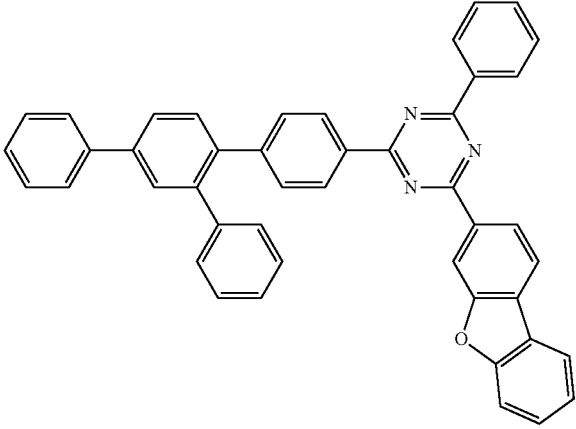 [SMILES: c1ccc(-c2ccc(-c3ccc(-c4nc(-c5ccccc5)nc(-c5ccc6c(c5)oc5ccccc56)n4)cc3)c(-c3ccccc3)c2)cc1] | −5.82 | −1.95 | 1.07 |
| MX2 | 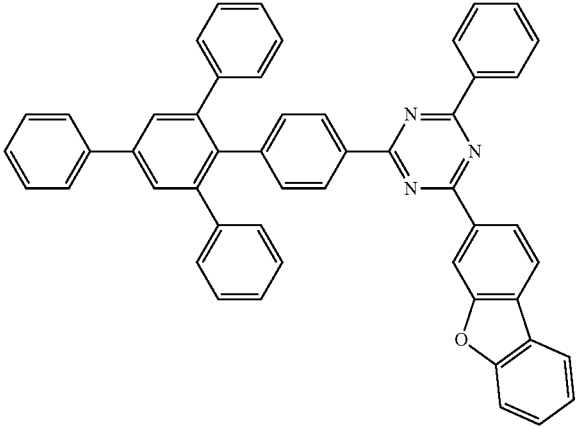 [SMILES: c1ccc(-c2cc(-c3ccccc3)c(-c3ccc(-c4nc(-c5ccccc5)nc(-c5ccc6c(c5)oc5ccccc56)n4)cc3)c(-c3ccccc3)c2)cc1] | −5.82 | −1.93 | 0.85 |

TABLE 1-continued

| Referred to as: | Structure | Calculated HOMO (eV) | Calculated LUMO (eV) | Dipole moment (Debye) |
|---|---|---|---|---|
| MX3 | 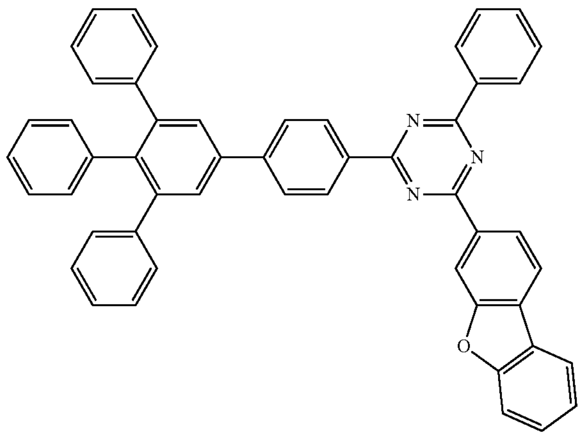 [SMILES: c1ccc(-c2nc(-c3ccc(-c4cc(-c5ccccc5)c(-c5ccccc5)c(-c5ccccc5)c4)cc3)nc(-c3ccc4c(c3)oc3ccccc34)n2)cc1] | −6.04 | −1.96 | 1.23 |
| MX4 | 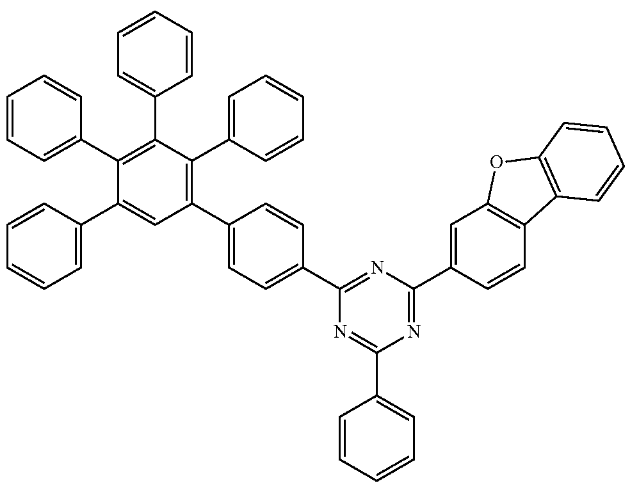 [SMILES: c1ccc(-c2nc(-c3ccc(-c4cc(-c5ccccc5)c(-c5ccccc5)c(-c5ccccc5)c4-c4ccccc4)cc3)nc(-c3ccc4c(c3)oc3ccccc34)n2)cc1] | −5.84 | −1.92 | 1.18 |
| MX5 | 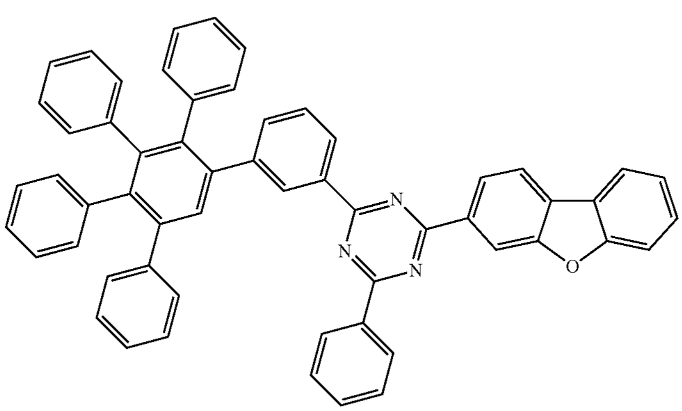 [SMILES: c1ccc(-c2nc(-c3cccc(-c4cc(-c5ccccc5)c(-c5ccccc5)c(-c5ccccc5)c4-c4ccccc4)c3)nc(-c3ccc4c(c3)oc3ccccc34)n2)cc1] | −5.83 | −1.91 | 0.80 |

TABLE 1-continued
| Referred to as: | Structure | Calculated HOMO (eV) | Calculated LUMO (eV) | Dipole moment (Debye) |
|---|---|---|---|---|
| MX6 | 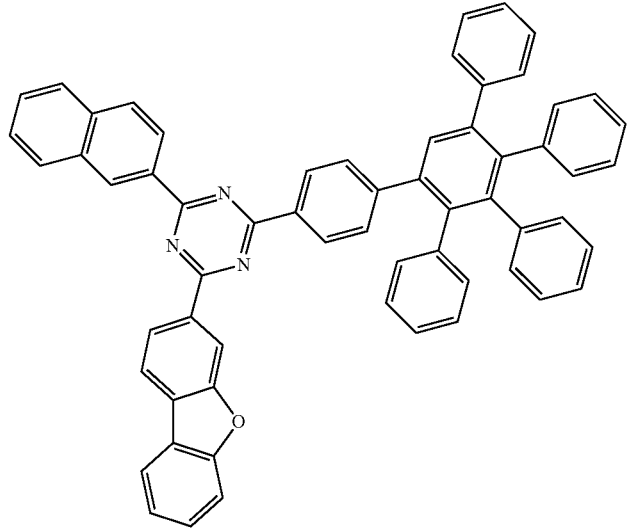 [SMILES: c1ccc(-c2cc(-c3ccc(-c4nc(-c5ccc6ccccc6c5)nc(-c5ccc6c(c5)oc5ccccc56)n4)cc3)c(-c3ccccc3)c(-c3ccccc3)c2-c2ccccc2)cc1] | −5.79 | −1.91 | 0.45 |
| MX7 | 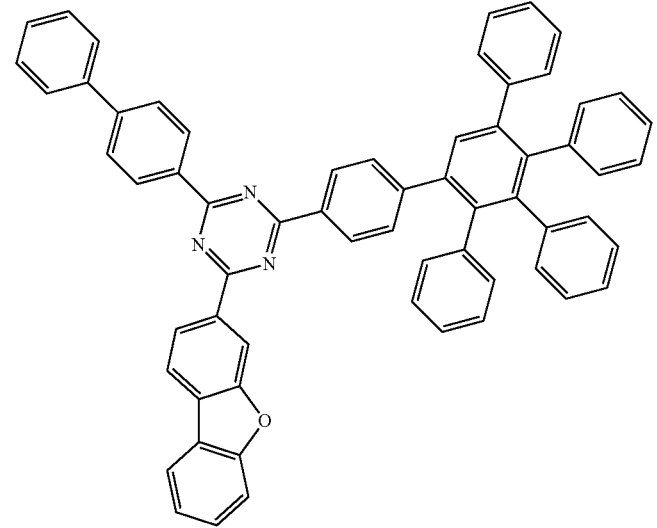 [SMILES: c1ccc(-c2ccc(-c3nc(-c4ccc(-c5cc(-c6ccccc6)c(-c6ccccc6)c(-c6ccccc6)c5-c5ccccc5)cc4)nc(-c4ccc5c(c4)oc4ccccc45)n3)cc2)cc1] | −5.84 | −1.91 | 0.89 |

TABLE 1-continued

| Referred to as: | Structure | Calculated HOMO (eV) | Calculated LUMO (eV) | Dipole moment (Debye) |
|---|---|---|---|---|
| MX8 | 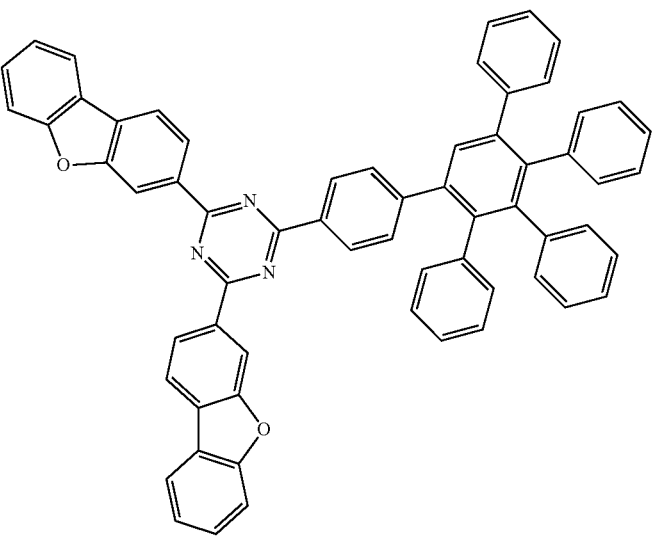 [SMILES: c1ccc(-c2cc(-c3ccc(-c4nc(-c5ccc6c(c5)oc5ccccc56)nc(-c5ccc6c(c5)oc5ccccc56)n4)cc3)c(-c3ccccc3)c(-c3ccccc3)c2-c2ccccc2)cc1] | −5.85 | −1.93 | 1.34 |
| MX9 | 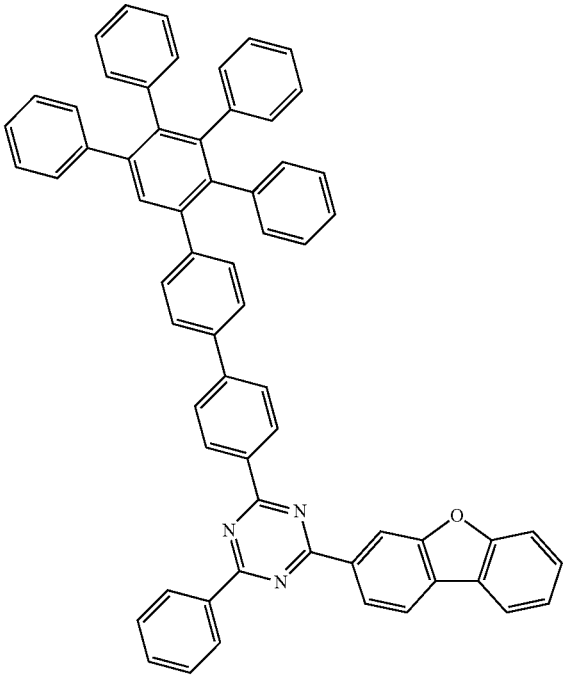 [SMILES: c1ccc(-c2nc(-c3ccc(-c4ccc(-c5cc(-c6ccccc6)c(-c6ccccc6)c(-c6ccccc6)c5-c5ccccc5)cc4)cc3)nc(-c3ccc4c(c3)oc3ccccc34)n2)cc1] | −5.72 | −1.95 | 1.43 |

General Procedure for Fabrication of OLEDs

For top emission devices, Examples 1 to 9 and comparative example 1, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare the substrate. 100 nm Ag were deposited on the substrate at a pressure of $10^{-5}$ to $10^{-7}$ mbar to form the anode.

Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 2,2',2''-(cyclopropane-1,2,3-triylidene)tris(2-(p-cyanotetrafluorophenyl)acetonitrile) was vacuum deposited on the anode, to form a HIL having a thickness of 10 nm. Then, Biphenyl-4-yl(9,9-diphenyl-9H-fluoren-2-yl)-[4-(9-phenyl-9H-carbazol-3-yl)phenyl]-amine was vacuum deposited on the HIL, to form a HTL having a thickness of 118 nm.

Then N,N-bis(4-(dibenzo[b,d]furan-4-yl)phenyl)-[1,1':4',1''-terphenyl]-4-amine (CAS 1198399-61-9) was vacuum deposited on the HTL, to form an electron blocking layer (EBL) having a thickness of 5 nm.

Then 97 vol.-% H09 (Sun Fine Chemicals) as EML host and 3 vol.-% BD200 (Sun Fine Chemicals) as fluorescent blue dopant were deposited on the EBL, to form a blue-emitting EML with a thickness of 20 nm.

Then the hole blocking layer is formed with a thickness of 5 nm by depositing 2,4-diphenyl-6-(4',5',6'-triphenyl-[1,1': 2',1''':3''',1''':3''',1''''-quinquephenyl]-3''''-yl)-1,3,5-triazine on the emission layer.

Then, the electron transporting layer is formed on the hole blocking layer according to Examples 1 to 9 and comparative example 1 with a the thickness of 31 nm. The electron transport layer comprises 50 wt.-% matrix compound and 50 wt.-% of alkali organic complex, see Table 2.

Then, the electron injection layer is formed on the electron transporting layer by deposing Yb with a thickness of 2 nm.

Ag is evaporated at a rate of 0.01 to 1 Å/s at $10^{-7}$ mbar to form a cathode with a thickness of 11 nm.

A cap layer of Biphenyl-4-yl(9,9-diphenyl-9H-fluoren-2-yl)-[4-(9-phenyl-9H-carbazol-3-yl)phenyl]-amine is formed on the cathode with a thickness of 75 nm.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured at 20° C. The current-voltage characteristic is determined using a Keithley 2635 source measure unit, by sourcing a voltage in V and measuring the current in mA flowing through the device under test. The voltage applied to the device is varied in steps of 0.1V in the range between 0V and 10V. Likewise, the luminance-voltage characteristics and CIE coordinates are determined by measuring the luminance in $cd/m^2$ using an Instrument Systems CAS-140CT array spectrometer for each of the voltage values. The cd/A efficiency at 10 mA/$cm^2$ is determined by interpolating the luminance-voltage and current-voltage characteristics, respectively.

Lifetime LT of the device is measured at ambient conditions (20° C.) and 30 mA/$cm^2$, using a Keithley 2400 sourcemeter, and recorded in hours.

The brightness of the device is measured using a calibrated photo diode. The lifetime LT is defined as the time till the brightness of the device is reduced to 97% of its initial value.

The light output in external efficiency EQE and power efficiency (1 m/W efficiency) are determined at 10 mA/$cm^2$ for top emission devices.

To determine the efficiency EQE in % the light output of the device is measured using a calibrated photodiode.

To determine the power efficiency in 1 m/W, in a first step the luminance in candela per square meter (cd/m2) is measured with an array spectrometer CAS140 CT from Instrument Systems which has been calibrated by Deutsche Akkreditierungsstelle (DAkkS). In a second step, the luminance is then multiplied by 7 and divided by the voltage and current density.

Top Emission Devices

In Table 2 is shown the performance of in organic electronic device comprising an organic semiconductor layer comprising triazine compound of formula 1 and an alkali organic complex.

In comparative example 1 compound ETM-1 was used as matrix compound:

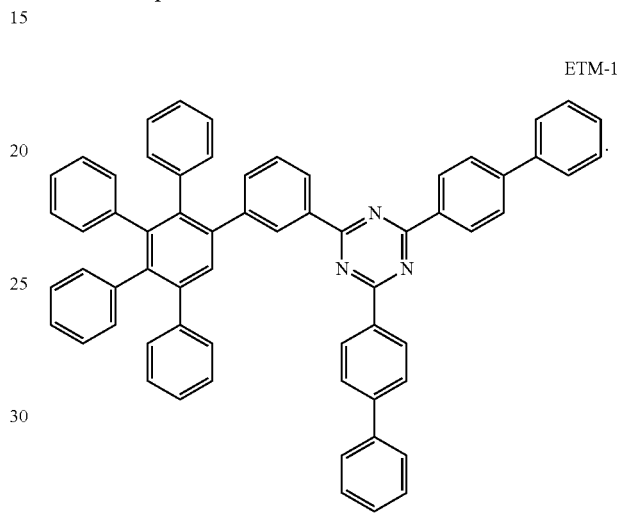

ETM-1

In comparative example 1, compound ETM-1 was used as matrix compound. The organic semiconductor layer comprises 50 vol.-% ETM-1 and 50 vol.-% LiQ. The operating voltage is 3.5 V and the cd/A efficiency is 8 cd/A. The lifetime is 37 hours.

In Example 1, the organic semiconductor layer comprises 50 vol.-% compound of formula 1 MX1 and 50 vol.-% LiQ. The operating voltage is 3.5 V. The cd/A efficiency is 8 cd/A and the lifetime is improved to 47 hours.

In Examples 2 to 9, further compounds of formula 1 have been tested in an organic semiconductor layer comprising 50 vol.-% compound of formula 1 and 50 vol.-% LiQ. The lifetime is always improved, see Table 2.

TABLE 2

Performance data of organic electroluminescent device comprising an organic semiconductor layer comprising triazine compound of formula 1 and an alkali organic complex

| | Matrix compound | Concentration of matrix compound (vol.-%) | Alkali organic complex | Concentration of alkali organic complex (vol.-%) | Thickness electron transport layer (nm) | Operating voltage at 10 mA/$cm^2$ (V) | cd/A efficiency at 10 mA/$cm^2$ (cd/A) | LT97 at 30 mA/$cm^2$ (h) |
|---|---|---|---|---|---|---|---|---|
| Comparative example 1 | ETM-1 | 50 | LiQ | 50 | 31 | 3.5 | 8.0 | 37 |
| Example 1 | MX1 | 50 | LiQ | 50 | 31 | 3.5 | 8.0 | 47 |
| Example 2 | MX2 | 70 | LiQ | 30 | 31 | 3.4 | 7.9 | 46 |
| Example 3 | MX3 | 50 | LiQ | 50 | 31 | 3.5 | 7.8 | 59 |
| Example 4 | MX4 | 50 | LiQ | 50 | 31 | 3.6 | 7.8 | 50 |
| Example 5 | MX5 | 50 | LiQ | 50 | 31 | 3.7 | 7.9 | 68 |
| Example 6 | MX6 | 50 | LiQ | 50 | 31 | 3.6 | 7.9 | 49 |
| Example 7 | MX7 | 70 | LiQ | 30 | 31 | 3.5 | 8.1 | 46 |

TABLE 2-continued

Performance data of organic electroluminescent device comprising an organic semiconductor layer comprising triazine compound of formula 1 and an alkali organic complex

|  | Matrix compound | Concentration of matrix compound (vol.-%) | Alkali organic complex | Concentration of alkali organic complex (vol.-%) | Thickness electron transport layer (nm) | Operating voltage at 10 mA/cm² (V) | cd/A efficiency at 10 mA/cm² (cd/A) | LT97 at 30 mA/cm² (h) |
|---|---|---|---|---|---|---|---|---|
| Example 8 | MX8 | 50 | LiQ | 50 | 31 | 3.5 | 7.7 | 68 |
| Example 9 | MX9 | 50 | LiQ | 50 | 31 | 3.5 | 8.0 | 47 |

Technical Effect of the Invention

As can be seen in Table 1 that the LUMO energy level (eV) of the compositions of examples 1 to 9 according to formula 1 are very low.

In summary, improved lifetime and more negative LUMO energy level (eV) may be achieved when the organic semiconductor layer comprises a triazine compound of formula 1. High performance may be achieved for a wide range of alkali organic complexes While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A triazine compound according to formula 1:

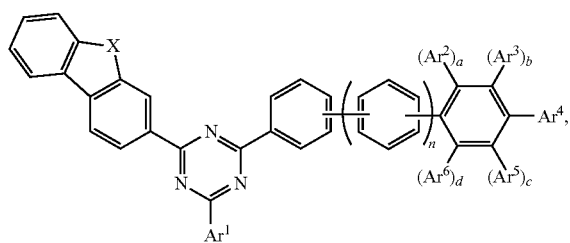

(1)

wherein
X is O, S or Se;
a, b, c, d are selected from 0 or 1, wherein 1≤a+b+c+d≤3;
n is selected from 0, 1 or 2,
$Ar^1$ is selected from $C_1$ to $C_{16}$ alkyl, substituted or unsubstituted $C_6$ to $C_{40}$ aryl, substituted or unsubstituted $C_3$ to $C_{40}$ heteroaryl, wherein
the substituents of the substituted $C_6$ to $C_{40}$ aryl and substituted $C_3$ to $C_{40}$ heteroaryl are selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, -PX($R^1$)$_2$, D, F or CN, wherein
$R^1$ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;
$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein
the substituent of the substituted $C_6$ to $C_{12}$ aryl or substituted $C_4$ to $C_{10}$ heteroaryl is selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN.

2. The triazine compound of formula 1 according to claim 1, wherein X is selected from O or S.

3. The triazine compound of formula 1 according to claim 1, wherein
$Ar^1$ is selected from $C_1$ to $C_{12}$ alkyl, substituted or unsubstituted $C_6$ to $C_{24}$ aryl or substituted or unsubstituted $C_3$ to $C_{36}$ heteroaryl, wherein
the substituents of the substituted $C_6$ to $C_{24}$ aryl and substituted $C_3$ to $C_{36}$ heteroaryl are selected from $C_1$ to $C_{12}$ alkyl, $C_1$ to $C_{12}$ alkoxy, partially or perfluorinated $C_1$ to $C_{12}$ alkyl, partially or perfluorinated $C_1$ to $C_{16}$ alkoxy, partially or perdeuterated $C_1$ to $C_{12}$ alkyl, partially or perdeuterated $C_1$ to $C_{16}$ alkoxy, $C_6$ to $C_{18}$ aryl, $C_3$ to $C_{25}$ heteroaryl, D, F or CN.

4. The triazine compound of formula 1 according to claim 1, wherein
$Ar^1$ is selected from the group comprising unsubstituted $C_6$ to $C_{24}$ aryl and $C_6$ or $C_{12}$ aryl.

5. The triazine compound of formula 1 according to claim 1, wherein $Ar^1$ is independently selected from B1 to B6, wherein
B1 to B6 are substituted or unsubstituted non-heteroaryl groups:

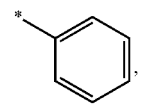

(B1)

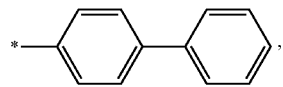

(B2)

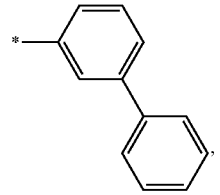

(B3)

-continued (B4)

(B5)

(B6)

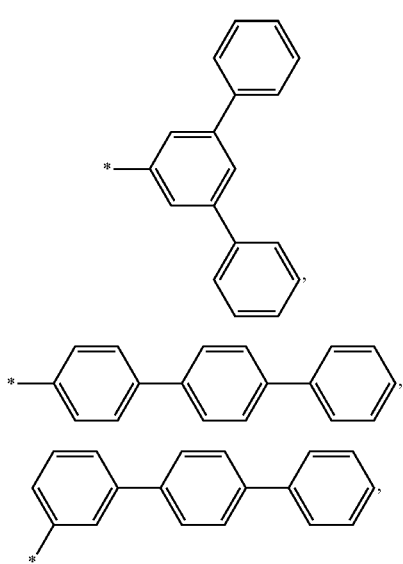

6. The triazine compound of formula 1 according to claim 1, wherein

Ar¹ may be independently selected from structures C1 to C5:

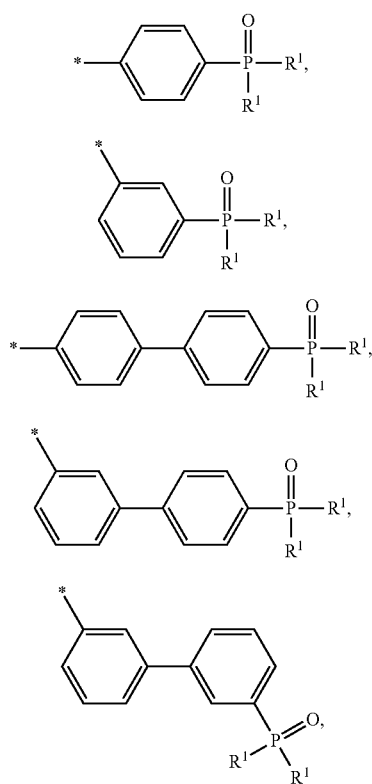

C1

C2

C3

C4

C5 wherein

R¹ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl.

7. The triazine compound of formula 1 according to claim 1, wherein at least one to at most three substituents of $Ar^2$, $Ar^3$, $Ar^5$ and $Ar^6$ are independently selected from unsubstituted $C_6$ to $C_{12}$ aryl or unsubstituted $C_4$ to $C_{10}$ heteroaryl phenyl, biphenyl, naphthyl, pyridyl, quinolinyl, quinazolinyl.

8. The triazine compound of formula 1 according to claim 1, wherein $Ar^4$ are independently selected from unsubstituted $C_6$ to $C_{12}$ aryl or unsubstituted $C_4$ to $C_{10}$ heteroaryl, phenyl, biphenyl, naphthyl, pyridyl, quinolinyl, quinazolinyl.

9. The triazine compound of formula 1 according to claim 1, wherein n=0 or 1.

10. The triazine compound of formula 1 according to claim 1, wherein a, b, c and d are selected from the group comprising a=1, b=0, c=0 and d=1,
a=0, b=0, c=0 and d=1,
a=0, b=0, c=1 and d=1,
a=0, b=1, c=1 and d=0, and
a=1, b=1, c=1 and d=0.

11. The triazine compound of formula 1 according to claim 1, wherein the triazine compound is selected from D1 to D9:

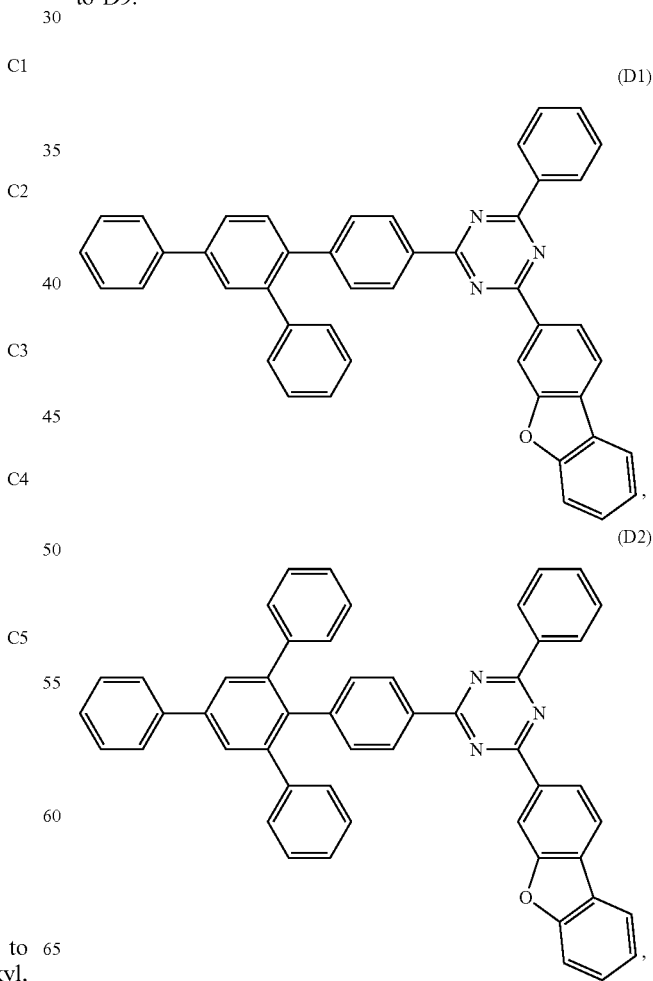

(D1)

(D2)

(D3)
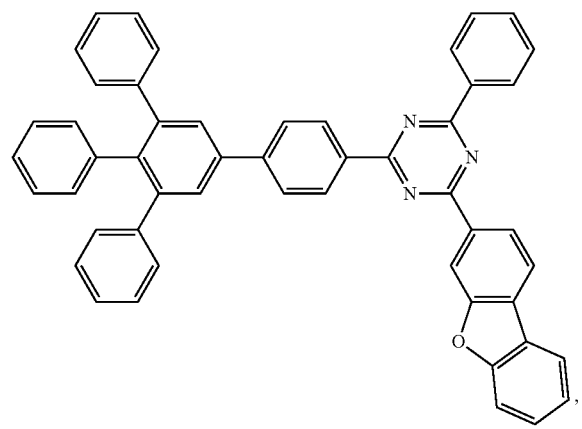
(D4)
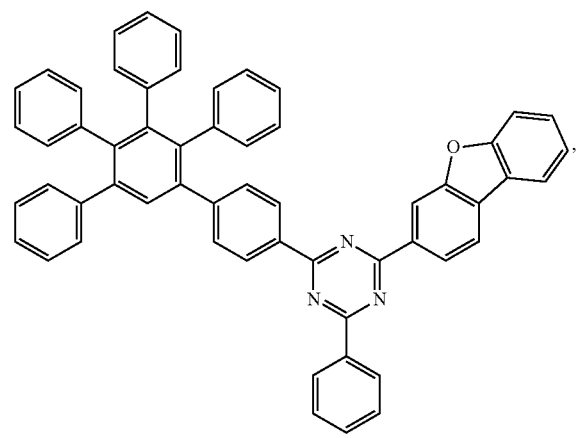
(D5)
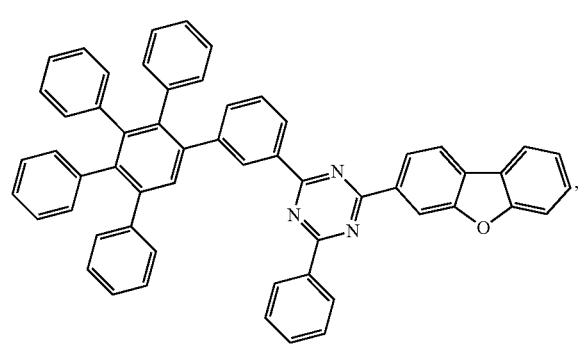
(D6)
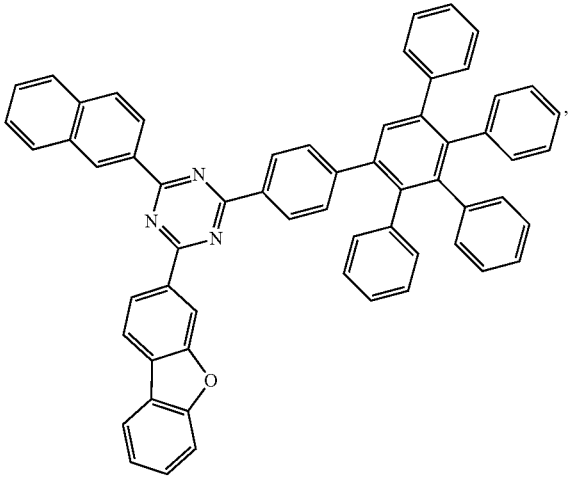
(D7)
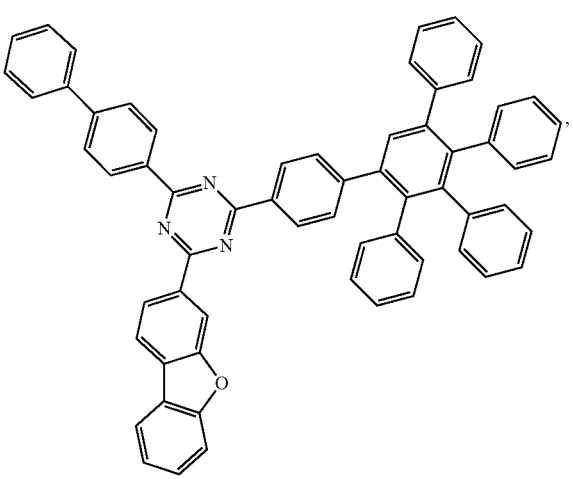
(D8)
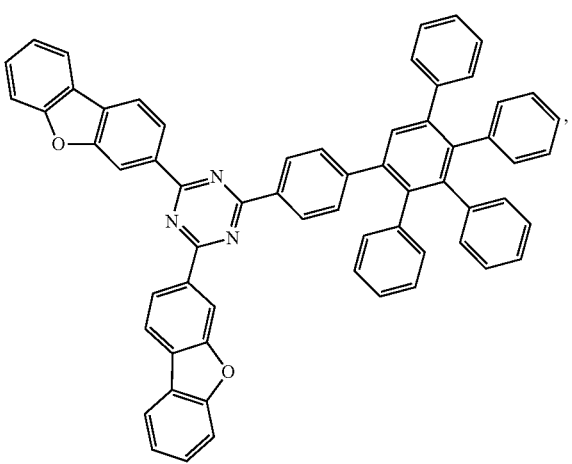

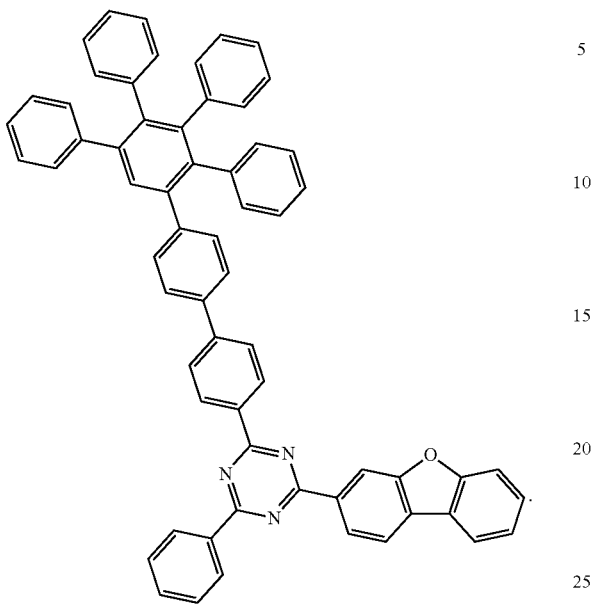
(D9)

12. An organic semiconductor layer comprising at least one triazine compound of formula 1 according to claim 1.

13. The organic semiconductor layer according to claim 12, further comprising a metal containing compound selected from the group comprising a metal, metal salt, organic metal complex, organic monovalent metal complex, divalent metal complex, LiQ and alkali borate.

14. An organic electronic device comprising an organic semiconductor layer according to claim 12, wherein at least one organic semiconductor layer comprises a triazine compound of formula 1.

15. The organic electronic device according to claim 14, wherein the electronic device is a light emitting device, thin film transistor, a battery, a display device or a photovoltaic cell.

16. The triazine compound of formula 1 according to claim 1, wherein $Ar^1$ is independently selected from B7 to B23, wherein B7 to B23 are substituted or unsubstituted annelated non-heteroaryl groups:

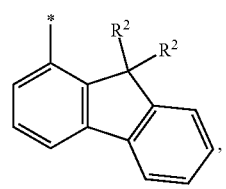
(B7)

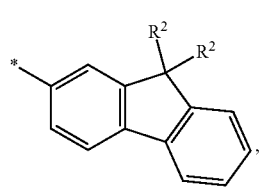
(B8)

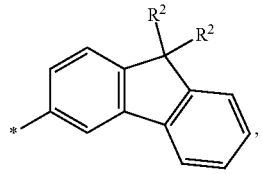
(B9)

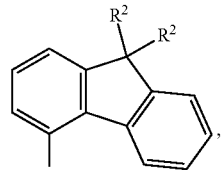
(B10)

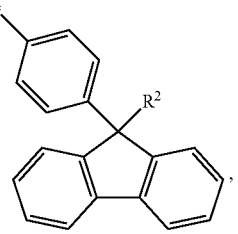
(B11)

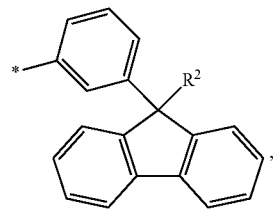
(B12)

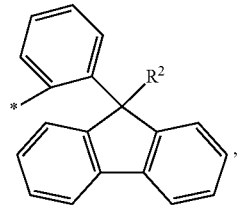
(B13)

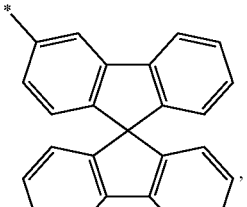
(B14)

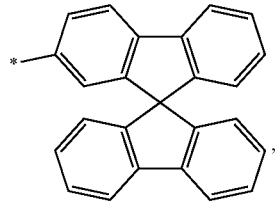
(B15)

-continued

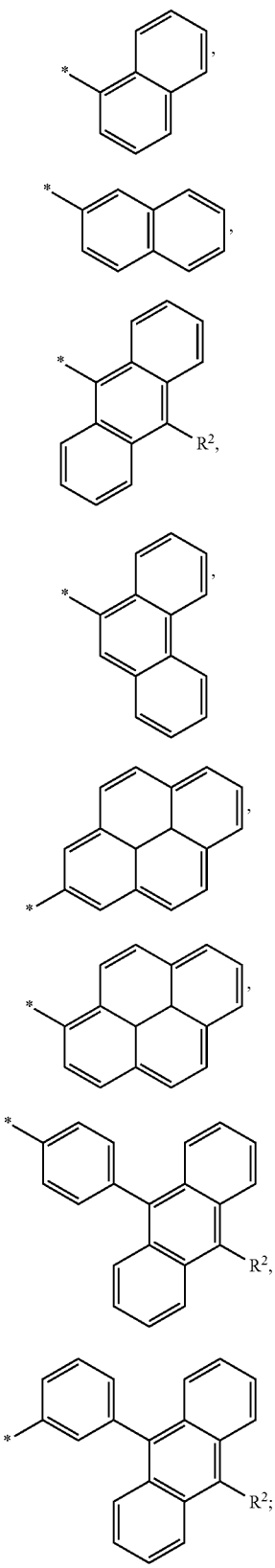

(B16), (B17), (B18), (B19), (B20), (B21), (B22), (B23)

wherein the substituent R² is independently selected from H, C₁ to C₁₆ alkyl, partially or perfluorinated C₁ to C₁₆ alkyl, partially or perdeuterated C₁ to C₁₆ alkyl, C₁ to C₁₆ alkoxy, C₃ to C₁₆ branched alkyl, C₃ to C₁₆ cyclic alkyl, C₃ to C₁₆ branched alkoxy, C₃ to C₁₆ cyclic alkoxy, C₆ to C₂₄ aryl and C₃ to C₂₅ heteroaryl.

17. The triazine compound of formula 1 according to claim 1, wherein Ar¹ is independently selected from B24 to B31, wherein B24 to B31 are selected from the group comprising a dibenzofurane or dibenzothiophene group:

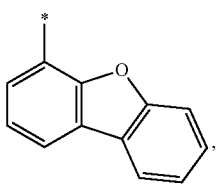
(B24)

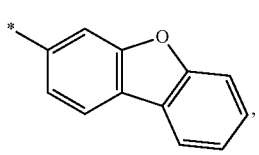
(B25)

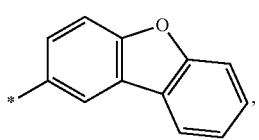
(B26)

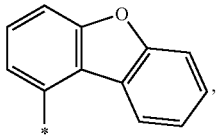
(B27)

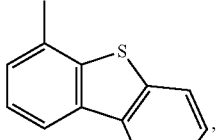
(B-28)

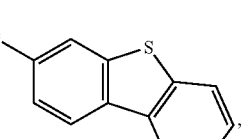
(B29)

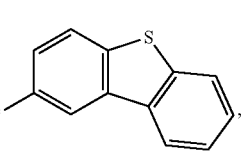
(B30)

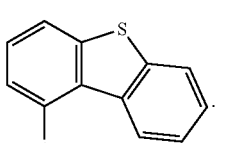
(B31)

18. The triazine compound of formula 1 according to claim 1, wherein Ar¹ is independently selected from B32 to B34, wherein B32 to B34 are unsubstituted pyridine groups:

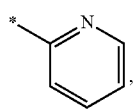 (B32)
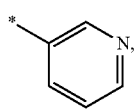 (B33)
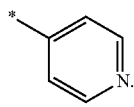 (B34)
19. The triazine compound of formula 1 according to claim 1, wherein Ar¹ is independently selected from B35 to B62, wherein B35 to B62 are unsubstituted or substituted hetero arylene groups:
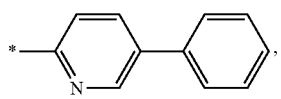 (B35)
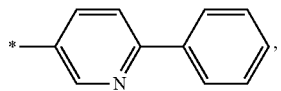 (B36)
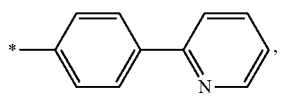 (B37)
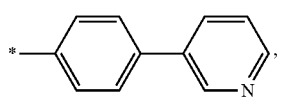 (B38)
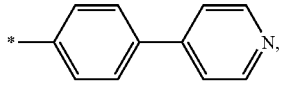 (B39)
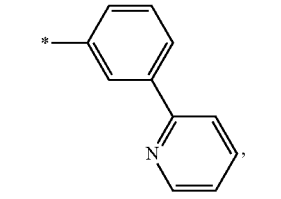 (B40)
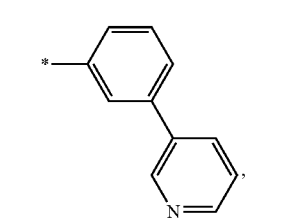 (B41)
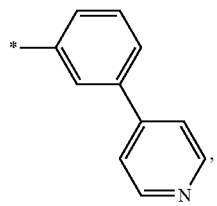 (B42)
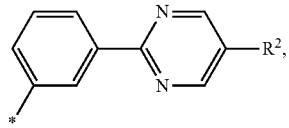 (B43)
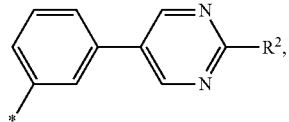 (B44)
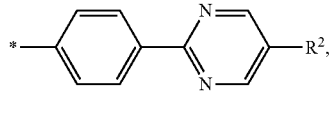 (B45)
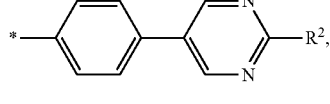 (B46)
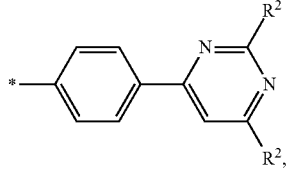 (B47)
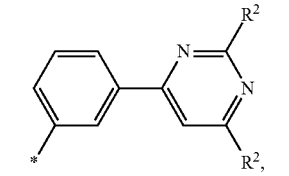 (B48)
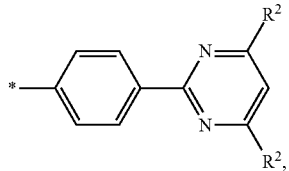 (B49)
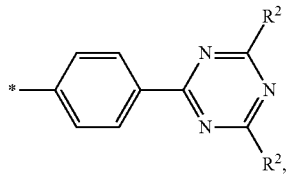 (B50)

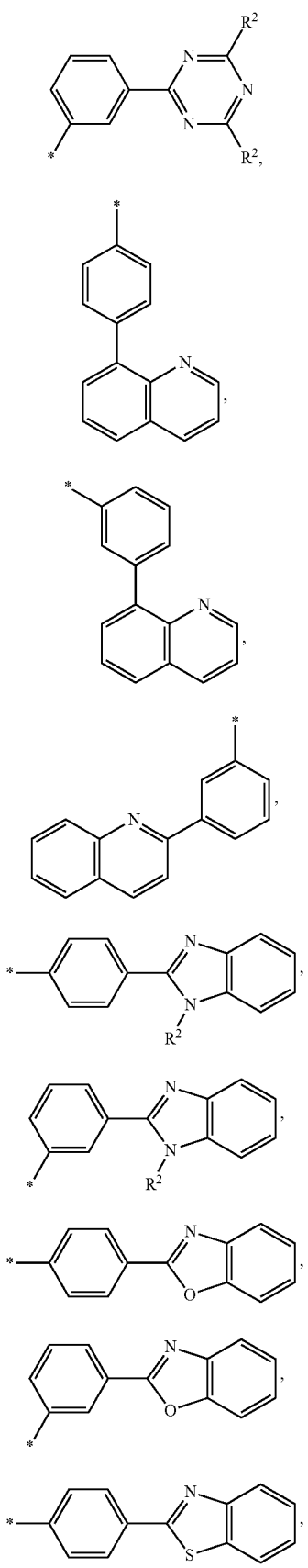

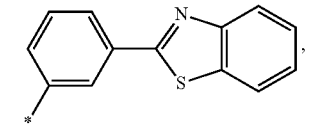

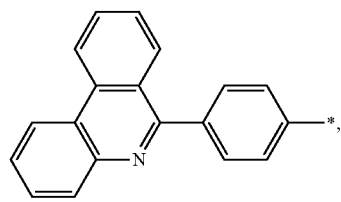

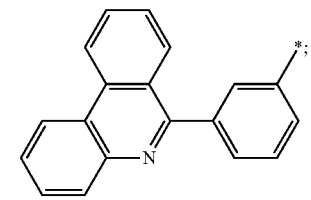

wherein the substituent $R^2$ is independently selected from H, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, $C_6$ to $C_{24}$ aryl and $C_3$ to $C_{25}$ heteroaryl.

20. The triazine compound of formula 1 according to claim 1, wherein $Ar^1$ is independently selected from B63 to B65, wherein B63 to B65 are unsubstituted annelated hetero arylene groups:

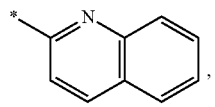

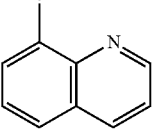

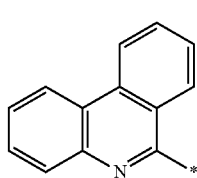

21. The triazine compound of formula 1 according to claim 1, wherein $Ar^1$ is independently selected from B66 to B67, wherein B66 and B67 are nitrile substituted phenyl groups:

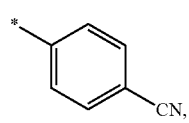

(B67) 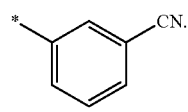

22. The triazine compound of formula 1 according to claim 1, wherein Ar¹ is independently selected from B68 to B70, wherein B68 to B70 are nitrile substituted biphenyl groups:

(B68) 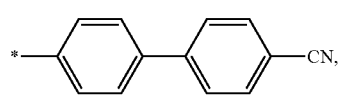

(B69) 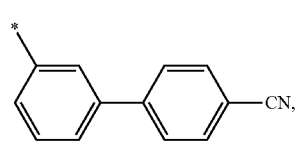

(B70) 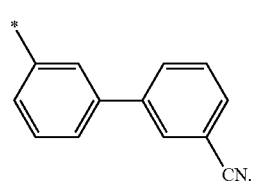

23. The triazine compound of formula 1 according to claim 1, wherein Ar¹ is independently selected from B71 to B77, wherein B71 to B77 are carbazole groups:

(B71) 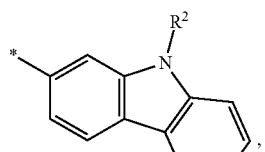

(B72) 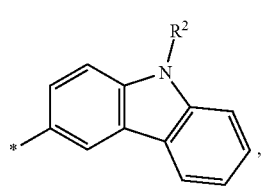

(B73) 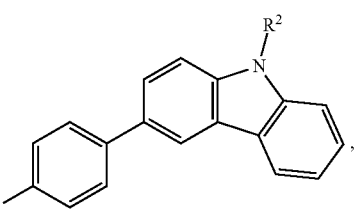

(B74) 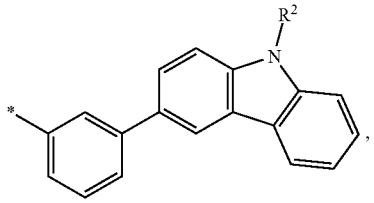

(B75) 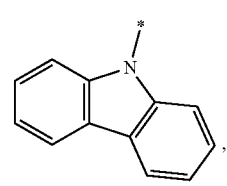

(B76) 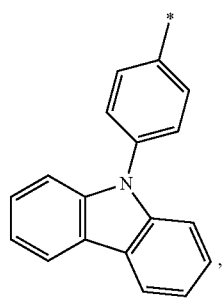

(B77) 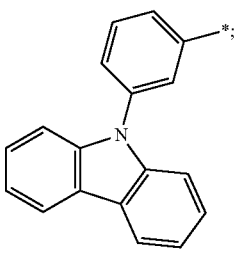

wherein
the substituent R² is independently selected from H, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, $C_6$ to $C_{24}$ aryl and $C_3$ to $C_{25}$ heteroaryl.

* * * * *